(12) United States Patent
Eldon et al.

(10) Patent No.: US 11,033,631 B2
(45) Date of Patent: Jun. 15, 2021

(54) METHODS OF TREATING CYP2D6 ALTERNATIVE METABOLIZERS

(75) Inventors: Michael A. Eldon, Redwood City, CA (US); C. Simone Jude-Fishburn, Redwood City, CA (US); Hema Gursahani, Foster City, CA (US); Myong Gyong Lee, Palo Alto, CA (US)

(73) Assignee: Nektar Therapeutics, San Francisco, CA (US)

( * ) Notice: Subject to any disclaimer, the term of this patent is extended or adjusted under 35 U.S.C. 154(b) by 928 days.

(21) Appl. No.: 12/993,807

(22) PCT Filed: Jun. 9, 2009

(86) PCT No.: PCT/US2009/003482
§ 371 (c)(1),
(2), (4) Date: Mar. 11, 2011

(87) PCT Pub. No.: WO2009/151590
PCT Pub. Date: Dec. 17, 2009

(65) Prior Publication Data
US 2011/0160186 A1 Jun. 30, 2011

Related U.S. Application Data

(60) Provisional application No. 61/131,569, filed on Jun. 9, 2008.

(51) Int. Cl.
| | | |
|---|---|---|
| A61K 31/155 | (2006.01) | |
| A61K 31/145 | (2006.01) | |
| A61K 8/43 | (2006.01) | |
| A61K 47/60 | (2017.01) | |
| A61P 9/12 | (2006.01) | |

(52) U.S. Cl.
CPC .................................. A61K 47/60 (2017.08)

(58) Field of Classification Search
CPC ........ A61K 47/60; A61K 8/43; A61K 31/145; A61K 31/155; A61K 31/415; A61P 9/12
See application file for complete search history.

(56) References Cited

U.S. PATENT DOCUMENTS

| 5,130,126 A | 7/1992 | Koyama et al. | |
|---|---|---|---|
| 5,672,662 A | 9/1997 | Harris et al. | |
| 2005/0136031 A1 | 6/2005 | Bentley et al. | |
| 2011/0009446 A1* | 1/2011 | Zhang et al. | ......... 514/307 |

FOREIGN PATENT DOCUMENTS

| WO | WO 02/40058 | 5/2002 |
|---|---|---|
| WO | WO 02/098949 | 12/2002 |
| WO | WO 2005/058367 | 6/2005 |
| WO | WO08/112257 | * 9/2008 |

OTHER PUBLICATIONS

Werner et al. Celecoxib inhibits metabolism of cytochrome P450 2D6 substrate metoprolol in humans. Clin. Pharmacol. Ther. 74, pp. 130-137 (2003).*

The Merck Index, 14th Edition, Merck & Co., Inc., p. THER-10 (2006).*
Berk, et al., "Effects of Pegylated Interferon Alfa-2B on the Pharmacokinetic and Pharmacodynamic Properties of Methadone: A Prospective, Nonrandomized, Crossover Study in Patients . . . ," Clin. Therap., vol. 29, No. 1, pp. 131-138, (2007).
Beverage, et al., "CYP2D6 Polymorphisms and the Impact on TamoxifenTherapy," J. of Pharm. Sci., vol. 96, No. 9, pp. 2224-2231, (Sep. 2007).
Chen, et al., "Synthesis and Properties of ABA Amphiphiles," J. Org. Chem., vol. 64, pp. 6870-6873, (1999).
De Leon, et al., "Med-Psych Drug-Drug Interactions Update: Clinical Guidelines for Psychiatrists for the Use of Pharmacogenetic Testing for CYP450 2D6 and CYP450 2C19," Psychosom., vol. 47, No. 1, pp. 75-85, (2006).
Ingelman-Sundberg, "Genetic polymorphisms of cytochrome P450 2D6 (CYP2D6): clinical consequences, evolutionary aspects and functional diversity," The Pharmacogen. J., vol. 5, pp. 6-13, (2005).
Kutscher, et al., "A Review of Drug Interactions With Psychiatric Medicines for the Pharmacy Practitioner," J. of Pharm. Prac., vol. 20, No. 4, pp. 327-333, (Aug. 2007).
Voet, et al., "Rates of Enzymatic Reactions," Biochemistry, 1st ed., John Wiley & Sons, Inc., New York, pp. 337, (1990).
Zanger, et al., "Cytochrome P450 2D6: overview and update on pharmacology, genetics, biochemistry," Naunyn-Schmiedeberg's Arch Pharmacol., vol. 369, No. 1, pp. 23-37, (2004).
Zhou, et al., "Substrate Specificity, Inhibitors and Regulation of Human Cytochrome P450 2D6 and Implications in Drug Development," Curr. Med. Chem., vol. 16, pp. 2661-2805, (2009).
PCT International Search Report corresponding to PCT Application No. PCT/US2009/003482 dated Dec. 2, 2009.
PCT International Preliminary Report on Patentability corresponding to PCT Application No. PCT/US2009/003482 dated Dec. 23, 2010.
Enzon Pharmaceuticals, Macromolecular Engineering Technologies, 16 pages, (2004).
NEKTAR™—Transforming Therapeutics, Nektar Molecule Engineering: Polyethylene Glycol and Derivatives for Advanced PEGylation, 24 pages, Catalog—2003, (Jul. 2003).
NEKTAR™—Transforming Therapeutics, Nektar Advanced PEGylation: Polyethylene Glycol and Derivatives for Advanced PEGylation, 27 pages, Catalog—2004, (Jul. 2004).
NEKTAR™—Transforming Therapeutics, Nektar Advanced PEGylation: Polyethylene Glycol and Derivatives for Advanced PEGylation, 33 pages, (Catalog 2005-2006).
NOF Corporation, PEG Derivatives, Phospholipid and Drug Delivery Materials for Pharmaceuticals, pp. 1-46, Catalogue 2003-1st, (Jan. 2003).
NOF Corporation, PEG Derivatives, Phospholipid and Drug Delivery Materials for Pharmaceuticals, pp. 1-50, Catalogue 2003-2nd, (Mar. 2004).

(Continued)

*Primary Examiner* — Jeffrey S Lundgren
*Assistant Examiner* — Chris E Simmons
(74) *Attorney, Agent, or Firm* — Jacqueline F. Mahoney

(57) ABSTRACT

The invention provides various methods comprising the administration of a CYP2D6 bioactive drug covalently bound to a water-soluble oligomer. Metabolism of CYP2D6 bioactive drug conjugates is diverted from CYP2D6 to alternative pathways, and the conjugates may therefore be utilized to alleviate the problems associated with interpopulation variation resulting from the genetic polymorphism in the CYP2D6 gene.

9 Claims, 9 Drawing Sheets

(56) References Cited

OTHER PUBLICATIONS

NOF Corporation, PEG Derivatives, Phospholipids and Drug Delivery Materials for Pharmaceutical Products and Formulations, 60 pages, Catalogue Ver. 8, (Apr. 2006).
Polypure 'Products, PEG amines; PEG acids and amino acids; PEG thiols and disulfides; BIOTINS, 5 pages, (Apr. 2004).
Polypure Products, PEG amines; PEG acids and amino acids; PEG thiols and disulfides; BIOTINS, 5 pages, (Apr. 2005).
Quanta Biodesign, Labeling, Derivatization and Crosslinking Reagents for Biological and Related Materials with dPEG™, pp. 1-38, (Mar. 12, 2004).
Quanta Biodesign, Labeling, Modification and Crosslinking Reagents incorporating our unique monodispersed dPEG™ Technology, pp. 1-31, (Nov. 5, 2004).
Quanta Biodesign, Ltd., Leading innovator, producer and provider of monodisperse discrete PEG™(dPEG™) derivatives, (Product Catalog), pp. 1-51, (Updated: Jul. 18, 2005).
Quanta Biodesign, Ltd., Leading innovator, producer and provider of monodisperse discrete PEG™(dPEG™) derivatives, (Product Catalog), pp. 1-51, (Updated: Nov. 17, 2005).
Shearwater Polymers, Inc., Polyethylene Glycol and Derivatives, 50 pages, (Catalog—Mar. 1995).
Shearwater Polymers, Inc., Polyethylene Glycol and Derivatives, 55 pages, (Catalog—Jul. 1997).
Shearwater Polymers, Inc., Polyethylene Glycol and Derivatives: Functionalized Biocompatible Polymers for Research and Pharmaceuticals, pp. 1-50, (Catalog—Jan. 2000).
Shearwater Corporation, Polyethylene Glycol and Derivatives for Biomedical Applications, 20 pages, (Catalog—Jul. 2001).

\* cited by examiner

METHODS OF TREATING CYP2D6 ALTERNATIVE METABOLIZERS

CROSS REFERENCE TO RELATED APPLICATIONS

This application is a 35 U.S.C. § 371 application of International Application No. PCT/US2009/003482, filed Jun. 9, 2009, designating the United States, which claims the benefit of priority under 35 U.S.C. § 119(e) to U.S. Provisional Patent Application Ser. No. 61/131,569, filed Jun. 9, 2008, both of which are incorporated herein by reference in their entireties.

BACKGROUND OF THE INVENTION

Field of the Invention

This application relates to the use of CYP2D6 bioactive compounds covalently bound to a water-soluble oligomer in the treatment of CYP2D6 alternative metabolizers as defined herein.

Description of the Related Art

The CYP2D6 isoform comprises only a small fraction of the total CYP450 hepatic enzyme content, yet it is of significant clinical importance, acting as the dominant metabolizing enzyme for approximately 20-25% of marketed drugs, including dextromethorphan, β-blockers (e.g., metoprolol), antiarrhythmics, anti-depressants (e.g., fluvoxamine, fluoxetine, imipramine, nortriptyline), antipsychotics (e.g., haloperidol, risperidone), morphine derivatives, and many other drugs. Various polymorphisms exist in the human population, however, which underlie different activities of the CYP2D6 isoform and the resulting inter-individual variation observed in drug metabolism. These polymorphisms have been well characterized, and the specific genetic mutations and/or duplications have been identified and correlated with the various metabolic phenotypes. Individuals expressing the different isoforms are categorized as poor metabolizers (PMs), intermediate metabolizers (IMs), extensive metabolizers (EMs), or ultrarapid metabolizers (UMs) based on the relative activity of the CYP2D6 enzyme that they express. (Beverage et al., *J. Pharm. Sci.,* 96:2224-2231 (2007); deLeon et al., *Psychosomatics,* 47:75-85 (2006)). The CYP2D6 genotype has successfully predicted the clearance of various drugs, including antidepressants such as desipramine and fluvoxamine and neuroleptics such as perphenazine, among others. (Ingelman-Sundberg, *Pharmacogenomics* 1, 5:6-13 (2005)).

PMs and IMs have no or reduced CYP2D6 activity, respectively. In these individuals, metabolism of selective CYP2D6 substrates occurs at a lower rate, or not at all; as a consequence, the risk for adverse drug reactions is higher in these populations. Due to elevated plasma levels of the administered drug, adverse events occur more frequently in PMs and IMs in cases where the drug clearance is dependent on CYP2D6. Moreover, the lack of CYP2D6 activity in PMs and the reduced CYP2D6 activity in IMs results in reduced effectiveness of drug administration where a prodrug requiring activation by CYP2D6 is used.

EMs have expected levels of CYP2D6 activity, and drugs metabolized by CYP2D6 undergo metabolism to a typical degree.

For UMs, metabolism of CYP2D6 bioactive drugs is enhanced. Subjects with multiple gene copies, for example, will metabolize drugs more rapidly than extensive metabolizers; as such, therapeutic plasma levels will not be achieved at ordinary doses in this population.

Thus the polymorphism of CYP2D6 significantly affects both the practicality and the efficacy of numerous drugs currently used clinically or under consideration for therapeutic use. In PMs and IMs, administration of a CYP2D6 bioactive drug may have no beneficial (or pharmacological) effect, and it may result in the buildup of the drug to toxic levels. In UMs, greater quantities of the drug must be administered to achieve therapeutic levels, translating into an increase in treatment costs of thousands of dollars a year per patient in the United States. Dosage levels of CYP2D6 bioactive drugs must be adjusted for CYP2D6 alternative metabolizers (i.e. PMs, IMs, and UMs) in order to compensate for altered CYP2D6 activity. Adverse drug-drug interactions are also a significant concern in CYP2D6 alternative metabolizers. Id.

Due to the complex nature of CYP2D6 metabolism, and the possibility of negative effects, candidate pharmaceuticals are typically screened for metabolism through CYP2D6. Those found to be largely subject to CYP2D6-mediated metabolism generally are not pursued.

SUMMARY OF THE INVENTION

In view of the foregoing, we have recognized a need to alter the metabolic pathway of drugs metabolized by CYP450 2D6 (CYP2D6) in order to reduce the population variability for these drugs that arises from the high polymorphism of CYP2D6. Metabolism through an alternate pathway would allow for a more widespread, predictable use of CYP2D6 bioactive drugs without the adverse effects associated with population-dependent metabolism through CYP2D6. Currently there is no known system for globally reducing the affinity of drugs for CYP2D6 while increasing the affinity for an alternative pathway without extensive medicinal chemistry that alters the overall pharmacodynamic properties of the drug.

To address the need in the art for diverting the metabolic pathway of CYP2D6 bioactive drugs, the present invention provides methods of treating CYP2D6 alternative metabolizers through the administration of an effective amount of a CYP2D6 bioactive drug covalently bound to a water-soluble oligomer. These conjugates show a reduction in affinity for the metabolic enzyme CYP2D6 and an increase in affinity for alternative pathways, where they are no longer subject to interpopulation variation resulting from the genetic polymorphism in the CYP2D6 gene.

Therefore, in one embodiment, the invention provides a method of treating a CYP2D6 alternative metabolizer having a disease treatable with a CYP2D6 bioactive drug, the method comprising administering to the CYP2D6 alternative metabolizer an effective amount of the drug covalently bound to a water-soluble oligomer.

In a further embodiment, the invention provides a method of modulating the efficacy of a CYP2D6 bioactive drug in a CYP2D6 alternative metabolizer, the method comprising administering to the CYP2D6 alternative metabolizer an effective amount of the drug covalently bound to a water-soluble oligomer.

In another embodiment, the invention provides a method of reducing drug-drug interactions in a CYP2D6 intermediate, extensive, or ultrarapid metabolizer, the method comprising co-administering to the metabolizer an effective amount of a CYP2D6 inhibiting drug covalently bound to a water-soluble oligomer with an effective amount of a CYP2D6 bioactive drug.

In a further embodiment, the invention provides a method of reducing drug-drug interactions in a CYP2D6 intermediate, extensive, or ultrarapid metabolizer, the method comprising co-administering to the metabolizer an effective amount of a CYP2D6 inhibiting drug with an effective amount of a CYP2D6 bioactive drug covalently bound to a water-soluble oligomer.

In one embodiment, the invention provides a method of identifying a candidate compound for administration to a CYP2D6 alternative metabolizer comprising assaying for the extent of metabolism of a test compound by CYP2D6; assaying for the extent of metabolism of the test compound covalently bound to a water-soluble oligomer by CYP2D6; and identifying a test compound as a candidate compound as one for which the degree of metabolism by CYP2D6 is less for the test compound covalently bound to a water-soluble oligomer than the test compound without the covalently bound water-soluble oligomer.

In another embodiment, the invention provides a compound comprising the formula D-X-POLY, wherein POLY is a water-soluble oligomer, preferably a polyethylene glycol (PEG) moiety, X is a spacer moiety, and D is a CYP2D6 bioactive drug, preferably a small molecule drug. In some instances, it is preferred that the CYP2D6 bioactive drug, D, is not a nucleotide, nucleoside, antihistamine, oxymorphone, platinum coordination complex based drug, steroid, fluoroquinolone, retinoid, phenothiazine, benzodiazepine, galactogugues, thiazide, amlodipine, nifedipine, nimodipine, 5-hydroxytryptophan, nevirapine, amifostine, amiodarone, aminocaproic acid, aminohippurate sodium, aminoglutethimide, aminolevulinic acid, aminosalicylic acid, amsacrine, anagrelide, anastrozole, asparaginase, anthracyclines, bexarotene, bicalutamide, bleomycin, buserelin, busulfan, cabergoline, capecitabine, carboplatin, carmustine, chlorambucin, cilastatin sodium, cladribine, clodronate, cyclophosphamide, cyproterone, cytarabine, camptothecins, dacarbazine, dactinomycin, daunorubicin, deferoxamine, diclofenac, docetaxel, doxorubicin, epirubicin, estramustine, etoposide, exemestane, fexofenadine, fludarabine, fluoxymesterone, flutamide, gemcitabine, epinephrine, L-Dopa, hydroxyurea, idarubicin, ifosfamide, imatinib, irinotecan, itraconazole, goserelin, letrozole, leucovorin, levamisole, lisinopril, lovothyroxine sodium, lomustine, mechlorethamine, melphalan, mercaptopurine, metaraminol bitartrate, methotrexate, metoclopramide, mexiletine, mitomycin, mitotane, mitoxantrone, nicotine, nilutamide, octreotide, pamidronate, pentostatin, pilcamycin, porfimer, procarbazine, prochlorperazine, ondansetron, raltitrexed, sirolimus, streptozocin, tacrolimus, tamoxifen, temozolomide, teniposide, tetrahydrocannabinol, thalidomide, thiotepa, topotecan, tretinoin, valrubicin, vinblastine, vincristine, vindesine, vinorelbine, dolasetron, granisetron; formoterol, leuprolide, amphotericin B, podophylotoxins, nucleoside antivirals, aroyl hydrazones or sumatriptan. In some embodiments, it is preferred that the CYP2D6 bioactive drug is one of the foregoing.

In a further embodiment, in a method of treating a disease in a CYP2D6 alternative metabolizer with a CYP2D6 bioactive drug comprising administering a therapeutically effective amount of the drug to the CYP2D6 alternative metabolizer, the invention provides an improvement comprising administering a therapeutically effective amount of the drug covalently bound to a water-soluble oligomer.

In one embodiment, in a method of treating one or more diseases in a CYP2D6 intermediate, extensive, or ultrarapid metabolizer with a CYP2D6 bioactive drug and a CYP2D6 inhibiting drug comprising co-administering to the CYP2D6 intermediate, extensive, or ultrarapid metabolizer a CYP2D6 bioactive drug and a CYP2D6 inhibiting drug, the invention provides an improvement comprising co-administering a therapeutically effective amount of the bioactive drug with a therapeutically effective amount of the inhibiting drug covalently bound to a PEG moiety.

These and other objects, aspects, embodiments and features of the invention will become more fully apparent when read in conjunction with the following detailed description.

DETAILED DESCRIPTION

Figure 1:
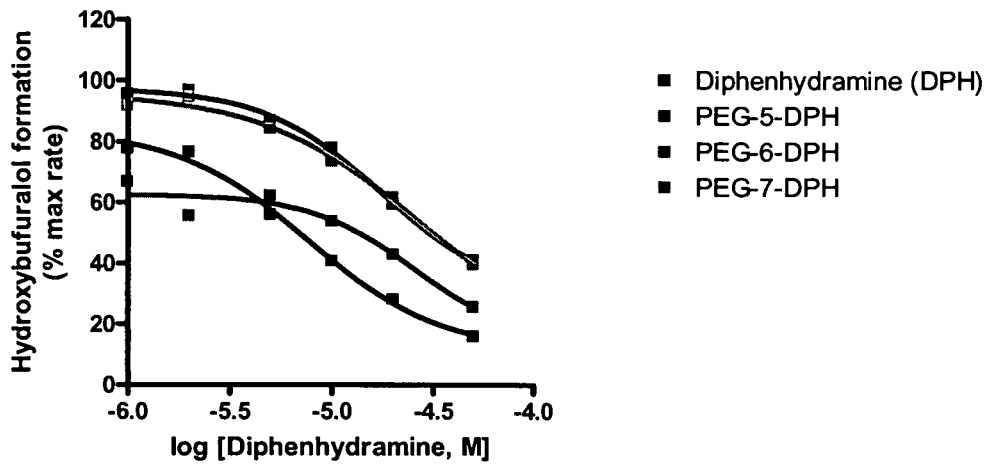
FIG. 1 shows the inhibition of CYP2D6 metabolism by diphenhydramine (DPH) and PEG-DPH. PEG conjugates show a decreased affinity for CYP2D6 versus unconjugated DPH.

As used in this specification, the singular forms "a," and "the" include plural referents unless the context clearly dictates otherwise.

In describing and claiming the present invention, the following terminology will be used in accordance with the definitions described below.

As used herein, the term "CYP2D6 alternative metabolizer" means any subject who is a poor metabolizer (PM), an intermediate metabolizer (IM) or an ultra metabolizer (UM) as understood in the art. Genetic analysis for CYP2D6 variations influencing drug metabolism is known in the art and can be used to predict, where necessary, whether a subject is a CYP2D6 alternative metabolizer or an extensive metabolizer. As used herein, "CYP2D6" refers to the 2D6 cytochrome P450 subtype.

The term "poor metabolizer" or "PM" is used herein is as it is used in the art, and refers to subjects who phenotypically have no CYP2D6 activity, and in whom metabolism or binding of CYP2D6 bioactive drugs occurs at an extraordinarily low rate or not at all. Genetically, as a non-limiting example, PMs typically have two nonfunctional alleles.

The term "intermediate metabolizer" or "IM" is used herein as it is used in the art, and refers to subjects who phenotypically have reduced levels of CYP2D6 activity, and in whom metabolism or binding of CYP2D6 bioactive drugs occurs at a lower than normal rate. As non-limiting examples, genetically IMs may have two reduced activity alleles or may be heterozygous for a nonfunctional allele and a decreased functional allele.

The term "extensive metabolizer" or "EM" is used herein as it is used in the art, and refers to subjects who phenotypically have expected CYP2D6 activity, and in whom metabolism or binding of CYP2D6 bioactive drugs occurs at a normal rate. As non-limiting examples, genetically EMs may have two functional alleles or one functional allele and one reduced function or nonfunctional allele.

The term "ultrarapid metabolizer" or "UM" is used herein as it is used in the art, and refers to subjects who have increased CYP2D6 activity, and in whom metabolism or binding of CYP2D6 bioactive drugs occurs at a greater than normal rate, specifically a rate faster than that of extensive metabolizers. As a non-limiting example, genetically UMs have more than two copies of functional alleles.

As used herein, the term "CYP2D6 bioactive drug" refers to a small molecule drug that, when administered therapeutically, interacts directly, at least in part, with the CYP450 2D6 isoform. CYP2D6 bioactive drugs may be metabolized by CYP2D6, and/or they may bind to CYP2D6. CYP2D6 bioactive drugs include, but are not limited to, CYP2D6 substrates, prodrugs, inhibitors, and inducers.

As used herein, a "CYP2D6 substrate" means a compound that is at least partially metabolized and/or otherwise altered by CYP2D6 upon administration of the CYP2D6 substrate to a patient. Thus, in some embodiments of the invention, a CYP2D6 substrate may be metabolized in its entirety, and in still other embodiments, a CYP2D6 substrate may be metabolized substantially or partially by CYP2D6. In certain embodiments of the invention, CYP2D6 is responsible for 100% of the metabolism of the CYP2D6 substrate. In other embodiments CYP2D6 is responsible for at least 95%, at least 90%, at least 85%, at least 80%, at least 75%, at least 70%, at least 65%, at least 60%, at least 55%, at least 50%, at least 45%, at least 40%, at least 35%, at least 30%, at least 25%, at least 20%, at least 15%, at least 10%, or at least 5% of the metabolism of the CYP2D6 substrate. CYP2D6 substrates include, but are not limited to, carvedilol, S-metoprolol, propafenone, timolol, amitriptyline, clomipramine, desipramine, imipramine, paroxetine, haloperidol, perphenazine, risperidone, thioridazine, zuclopenthixol, alprenolol, amphetamine, aripiprazole, atomoxetine, bufuralol, chlorpheniramine, chlorpromazine, codeine, debrisoquine, dexfenfluramine, dextromethorphan, duloxetine, encamide, flecamide, fluoxetine, fluvoxamine, lidocaine, metoclopramide, methoxyamphetamine, mexilletine, minaprine, nebivolol, nortriptyline, ondansetron, oxycodone, perhexyline, phenacetin, phenformin, promethazine, propranolol, sparteine, tamoxifen, tramadol, and venlafaxine.

As used herein, a "CYP2D6 inhibitor" is a small molecule drug that reduces the rate of metabolism of a CYP2D6 substrate by CYP2D6. CYP2D6 inhibitors include, but are not limited to, amiodarone, bupropion, celecoxib, chlorpheniramine, chlorpromazine, cimetidine, cinacalcet, citalopram, clemastine, clomipramine, cocaine, diphenhydramine, doxepin, doxorubicin, duloxetine, escitalopram, fluoxetine, goldenseal, halofantrine, histamine H1 receptor antagonists, hydroxyzine, levomepromazine, methadone, metoclopramide, mibefradil, midodrine, moclobemide, paroxetine, perphenazine, quinidine, ranitidine, red-haloperidol, ritonavir, sertraline, terbinafine, ticlopidine, and tripelennamine.

As used herein, a "small molecule drug" is a pharmacologically active compound having a molecular weight of less than about 1000 Daltons. Thus, small molecule drugs, for the purpose of the invention, include oligopeptides, oligonucleotides, and other biomolecules having a molecular weight of less than about 1000 Daltons. Also encompassed in the term "small molecule drug" is any fragment of a peptide, protein or antibody, including native sequences and variants falling within the molecular weight range stated above. In one or more embodiments, however, it is preferred that the small molecule drug satisfies one or more of the following: not an oligopeptide; not an oligonucleotide; not an antibody; and not a fragment of any of the foregoing.

The term "prodrug" as used herein means a drug that is pharmacologically inactive, but is modified by CYP2D6 to a pharmacologically active state. An "inducer" is molecule that increases the rate of metabolism of a CYP2D6 substrate.

It will be understood by one of skill in the art that a CYP2D6 bioactive drug may fall within one or more of the categories recited above. A drug may, for example, be both an inhibitor of CYP2D6 and a substrate of CYP2D6.

As used herein, a "disease treatable with a CYP2D6 bioactive drug" refers to any disease, disorder, or condition that may be alleviated, in part or in whole, in a subject in need thereof through the administration of a therapeutically effective amount of a CYP2D6 bioactive drug.

"Water-soluble oligomer" indicates a non-peptidic oligomer that is at least 35% (by weight) soluble, and preferably greater than 95% soluble, in water at room temperature. Typically, an unfiltered aqueous preparation of a "water-soluble" oligomer transmits at least 75%, more preferably at least 95%, of the amount of light transmitted by the same solution after filtering. On a weight basis, a "water-soluble" oligomer is preferably at least 35% (by weight) soluble in water, more preferably at least 50% (by weight) soluble in water, still more preferably at least 70% (by weight) soluble in water, and still more preferably at least 85% (by weight) soluble in water. It is most preferred, however, that the water-soluble oligomer is at least 95% (by weight) soluble in water or completely soluble in water.

An "oligomer" is a molecule possessing from about 1 to about 30 monomers. The architecture of an oligomer can vary. Specific oligomers for use in the invention include those having a variety of geometries such as linear, branched, or forked, to be described in greater detail below.

The terms "monomer," "monomeric subunit" and "monomeric unit" are used interchangeably herein and refer to one of the basic structural units of a polymer or oligomer. In the case of a homo-oligomer, this is defined as a structural repeating unit of the oligomer. In the case of a co-oligomer, a monomeric unit is more usefully defined as the residue of a monomer which was oligomerized to form the oligomer, since the structural repeating unit can include more than one type of monomeric unit. Preferred oligomers of the invention are homo-oligomers.

"PEG," "polyethylene glycol," or "PEG moiety," as used herein, is meant to encompass any water-soluble poly(ethylene oxide). Unless otherwise indicated, a "PEG oligomer" or an oligoethylene glycol is one in which substantially all (preferably all) monomeric subunits are ethylene oxide subunits, though the oligomer may contain distinct end capping moieties or functional groups, e.g., for conjugation. Typically, PEG oligomers for use in the present invention will comprise one of the two following structures: "—$(CH_2CH_2O)_n$—" or "—$(CH_2CH_2O)_{n-1}CH_2CH_2$—," depending upon whether or not the terminal oxygen(s) has been displaced, e.g., during a synthetic transformation. As stated above, for the PEG oligomers, the variable (n) ranges from 1 to 30, and the terminal groups and architecture of the overall PEG can vary. When PEG further comprises a functional group, A, for linking to, e.g., a small molecule drug, the functional group when covalently attached to a PEG oligomer, does not result in formation of (i) an oxygen-oxygen bond (—O—O—, a peroxide linkage), or (ii) a nitrogen-oxygen bond (N—O, O—N).

An "end capping group" is generally a non-reactive carbon-containing group attached to a terminal oxygen of a PEG oligomer. For the purposes of the present invention, preferred are capping groups having relatively low molecular weights such as methyl or ethyl. The end-capping group can also comprise a detectable label. Such labels include, without limitation, fluorescers, chemiluminescers, moieties used in enzyme labeling, colorimetric labels (e.g., dyes), metal ions, and radioactive moieties.

"Branched," in reference to the geometry or overall structure of an oligomer, refers to an oligomer having two or more polymer "arms" extending from a branch point.

"Forked" in reference to the geometry or overall structure of an oligomer, refers to an oligomer having two or more functional groups (typically through one or more atoms) extending from a branch point.

A "branch point" refers to a bifurcation point comprising one or more atoms at which an oligomer branches or forks from a linear structure into one or more additional arms.

"Substantially" or "essentially" means nearly totally or completely, for instance, 95% or greater, more preferably 97% or greater, still more preferably 98% or greater, even more preferably 99% or greater, yet still more preferably 99.9% or greater, with 99.99% or greater being most preferred of some given quantity.

"Monodisperse" refers to an oligomer composition wherein substantially all of the oligomers in the composition have a well-defined, single (i.e., the same) molecular weight and defined number of monomers, as determined by chromatography or mass spectrometry. Monodisperse oligomer compositions are in one sense pure, that is, substantially having a single and definable number (as a whole number) of monomers rather than a large distribution. A monodisperse oligomer composition possesses a MW/Mn value of 1.0005 or less, and more preferably, a MW/Mn value of 1.0000. By extension, a composition comprised of monodisperse conjugates means that substantially all oligomers of all conjugates in the composition have a single and definable number (as a whole number) of monomers rather than a large distribution and would possess a MW/Mn value of 1.0005, and more preferably a MW/Mn value of 1.0000 if the oligomer were not attached to the moiety derived from a small molecule drug. A composition comprised of monodisperse conjugates can, however, include one or more nonconjugate substances such as solvents, reagents, excipients, and so forth. In a preferred embodiment of the invention, the water-soluble oligomers are monodisperse.

"Bimodal," in reference to an oligomer composition, refers to an oligomer composition wherein substantially all oligomers in the composition have one of two definable and different numbers (as whole numbers) of monomers rather than a large distribution, and whose distribution of molecular weights, when plotted as a number fraction versus molecular weight, appears as two separate identifiable peaks. Preferably, for a bimodal oligomer composition as described herein, each peak is symmetric about its mean, although the size of the two peaks may differ. Ideally, the polydispersity index of each peak in the bimodal distribution, Mw/Mn, is 1.01 or less, more preferably 1.001 or less, and even more preferably 1.0005 or less, and most preferably a MW/Mn value of 1.0000. By extension, a composition comprised of bimodal conjugates means that substantially all oligomers of all conjugates in the composition have one of two definable and different numbers (as whole numbers) of monomers rather than a large distribution and would possess a MW/Mn value of 1.01 or less, more preferably 1.001 or less and even more preferably 1.0005 or less, and most preferably a MW/Mn value of 1.0000 if the oligomer were not attached to the moiety derived from a small molecule drug. A composition comprised of bimodal conjugates can, however, include one or more nonconjugate substances such as solvents, reagents, excipients, and so forth.

"Pharmaceutically acceptable excipient" or "pharmaceutically acceptable carrier" refers to an excipient that can be included in the compositions of the invention and that causes no significant adverse toxicological effects to the patient.

"Pharmacologically effective amount," "physiologically effective amount," and "therapeutically effective amount" are used interchangeably herein to mean the amount of a water-soluble oligomer-small molecule drug conjugate present in a composition that is needed to provide a desired level of active agent and/or conjugate in the bloodstream or in the target tissue. The precise amount will depend upon numerous factors, e.g., the particular active agent, the components and physical characteristics of the composition, intended patient population, patient considerations, and the like, and can readily be determined by one skilled in the art, based upon the information provided herein and available in the relevant literature.

A "difunctional" oligomer is an oligomer having two functional groups contained therein, typically at its termini. When the functional groups are the same, the oligomer is said to be homodifunctional. When the functional groups are different, the oligomer is said to be heterobifunctional.

The term "patient" or "subject" refers to a living organism, including both humans and animals, suffering from or prone to a condition that can be prevented or treated by administration of a CYP2D6 bioactive drug, or a conjugate thereof as described herein, including but not limited to water-soluble oligomer-small molecule drug conjugates.

"Optional" or "optionally" means that the subsequently described circumstance may or may not occur, so that the description includes instances where the circumstance occurs and instances where it does not.

In accordance with the invention, and as will be shown in further detail below and in the Examples, it has been found that conjugation of CYP2D6 bioactive drugs with one or more water-soluble oligomers diverts the metabolism of the drugs from CYP2D6 to alternative metabolic pathways and reduces the affinity of CYP2D6 inhibitors or inducers for CYP2D6. In this manner, the difficulties and adverse effects associated with the administration of a CYP2D6 bioactive drug and arising from the high polymorphism of CYP2D6 can be avoided, while retaining the therapeutic effectiveness of the drugs. In certain preferred embodiments of the invention, the water-soluble oligomers are PEG moieties.

As indicated above, the present invention is directed to (among other things) a method of treating a CYP2D6 alternative metabolizer having a disease treatable with a CYP2D6 bioactive drug, the method comprising administering to the CYP2D6 alternative metabolizer an effective amount of the drug covalently bound to a water-soluble oligomer. In one embodiment of this aspect of the invention, the water-soluble oligomer is a PEG moiety. The PEG moiety preferably comprises 5, 6, 7, or 8 polyethylene glycol subunits.

In another embodiment of this aspect of the invention, the CYP2D6 alternative metabolizer is a PM. In a further embodiment, the CYP2D6 alternative metabolizer is an IM. In another embodiment, the CYP2D6 alternative metabolizer is a UM.

In another embodiment of this aspect of the invention, the CYP2D6 bioactive drug is a CYP2D6 substrate. It will be understood by one of skill in the art that in this embodiment of the invention, administration of a CYP2D6 substrate covalently bound to a water-soluble oligomer will have a beneficial effect on all CYP2D6 alternative metabolizers, albeit in a different manner for each class of alternative metabolizers. PMs, for example, are unable to metabolize CYP2D6 substrates. As such, CYP2D6 substrates may build up to toxic levels in PMs. Diversion of metabolism of CYP2D6 bioactive drugs from CYP2D6 to alternative metabolic pathways, through the administration of the CYP2D6 substrate covalently bound to a water-soluble oligomer, will ensure metabolism of the drug, thereby avoiding toxic buildup. PMs, previously unable to metabolize the drug, would then be able to take the drug as it will be metabolized through other pathways. Similarly, IMs are only able to metabolize CYP2D6 substrates at a low rate, and CYP2D6 substrates may build up to toxic levels in IMs as well. Thus diversion of metabolism of CYP2D6 bioactive drugs to alternative metabolic pathways will enable IMs, previously unable to adequately metabolize CYP2D6 substrates, to take such drugs as they will be metabolized through other pathways. In UMs, CYP2D6 bioactive drugs are metabolized at a greater than normal rate, such that effective concentrations in the plasma cannot be achieved, or can only be achieved at very high doses. By conjugating the CYP2D6 bioactive drug to a water-soluble oligomer, rapid metabolism will be avoided, leading to sufficient plasma concentrations for efficacy, enabling UMs to take these drugs successfully. CYP2D6 substrates conjugated to a water-soluble oligomer may also be administered to EMs, however in this population, the benefit of doing so will not likely be associated with a change in CYP2D6-based metabolism.

The present invention is also directed to (among other things) a method of modulating the efficacy of a CYP2D6 bioactive drug in a CYP2D6 alternative metabolizer, the method comprising administering to the CYP2D6 alternative metabolizer an effective amount of the drug covalently bound to a water-soluble oligomer. As previously noted, the efficacy of a CYP2D6 bioactive drug can be diminished in an alternative metabolizer. In a non-limiting example, an ultrarapid metabolizer may rapidly inactivate a standard dose of a CYP2D6 bioactive drug, resulting in a lower plasma level, and lower efficacy of the drug relative to normal metabolizers. Efficacy of the drug may be achieved by administering to the alternative metabolizer an effective amount of the drug covalently bound to a water-soluble oligomer. As demonstrated herein, such conjugates are diverted from the CYP2D6 metabolic pathway, neutralizing the reduced efficacy seen in administration of the drug to alternative metabolizers. In the example of an ultrarapid metabolizer, a slower rate of metabolism may be achieved, allowing for sufficient build up of plasma levels of the drug and effective treatment of the patient.

It will be understood that the administration of a drug covalently bound to a water-soluble oligomer may also be beneficial where the drug is a prodrug activated by CYP2D6. In EMs, the prodrug is converted to its active species at a moderate rate. If the drug in question has a narrow therapeutic index, toxic levels of the active species may be achieved too rapidly. Administration of the drug covalently bound to a water-soluble oligomer will reduce the rate at which the prodrug is converted to its active species, and may enable an improved pharmacokinetic profile that avoids reaching toxic concentrations. In EMs and UMs, a prodrug activated by CYP2D6 may be rapidly converted to its active species, and peak concentrations reached may be toxic. This rate may be slowed through the administration of the drug covalently bound to a water-soluble oligomer, which may produce an improved pharmacokinetic profile that avoids reaching toxic concentrations.

In another embodiment, the present invention is directed to (among other things) a method of reducing drug-drug interactions in a CYP2D6 intermediate, extensive, or ultrarapid metabolizer, the method comprising co-administering an effective amount of a CYP2D6 inhibiting drug covalently bound to a water-soluble oligomer with an effective amount of a CYP2D6 bioactive drug.

It is well known that the co-administration of a CYP2D6 inhibitor with a CYP2D6 substrate can lead to an adverse drug-drug interaction (DDI). In particular, high affinity CYP2D6 inhibitors that bind strongly with CYP2D6 block metabolism of the co-administered CYP2D6 substrate, leading to unexpectedly high, and potentially toxic, plasma levels of the CYP2D6 substrate. EMs and UMs are subject to these adverse DDIs as they exhibit expected or increased CYP2D6 activity. IMs may also be subject to these adverse DDIs, as they retain some CYP2D6 activity. As demonstrated herein, conjugates of CYP2D6 inhibitors covalently bound to a water-soluble oligomer exhibit a reduced affinity for CYP2D6. As such, it is possible to alleviate any adverse DDIs associated with the co-administration a CYP2D6 inhibitor and a CYP2D6 substrate through the administration of the CYP2D6 inhibitor as a conjugate covalently bound to a water-soluble oligomer.

In a further embodiment, the invention provides a method of reducing drug-drug interactions in a CYP2D6 intermediate, extensive, or ultrarapid metabolizer, the method comprising co-administering to the IM, EM or UM an effective amount of a CYP2D6 inhibiting drug with an effective amount of a CYP2D6 bioactive drug covalently bound to a water-soluble oligomer. As described above, IMs, EMs, and UMs may be subject to adverse DDIs upon co-administration of a CYP2D6 inhibitor and a CYP2D6 substrate. It will be understood that these adverse DDIs can be moderated through the co-administration of a CYP2D6 inhibitor and a conjugate of the CYP2D6 substrate covalently bound to a water-soluble oligomer. As demonstrated herein, the conjugation of a CYP2D6 substrate to a water-soluble oligomer diverts metabolism of the CYP2D6 substrate from CYP2D6 to an alternative metabolic pathway, mitigating any adverse DDIs The degree of a given molecule's metabolism by and affinity for CYP2D6 and other CYP isoforms may be assessed by any techniques known in the art, including through the use of Bactosomes™ or by microsomal inhibition studies. In vitro metabolism studies using Bactosomes™ expressing individual human CYP isoforms monitor the extent to which a test compound is metabolized by a single CYP450 enzyme and allow identification of the CYP isoforms that may be responsible for the metabolism of a test compound. CYP450 microsomal inhibition assays identify and quantify the extent that a test compound inhibits key cytochrome P450 enzymes in liver microsomes. These techniques can be used to assess the metabolism and affinity of not only the unconjugated version of a CYP2D6 bioactive drug but conjugated versions as well.

In accordance with the present invention, and as demonstrated herein, conjugation of a CYP2D6 bioactive drug to a water-soluble oligomer, including but not limited to a PEG moiety, results in a diversion of metabolism of the drug from CYP2D6 to a different metabolic pathway, or reduced affinity for the drug by CYP2D6. Metabolism may be diverted to any pathway, including to any non-CYP2D6 CYP isoform pathway, any non-CYP pathway, or any combination thereof. In particular, metabolism of a CYP2D6 metababolizable drug covalently bound to a water-soluble oligomer may occur through any one or more of CYP3A4, CYP2C9, CYP2C19, CYP1A2, CYP2E1, CYP2A6, CYP1B1, CYP1A1, CYP2J2, CYP4F2, CYP2R1, CYP2A7, CYP7A1, CYP4A11, CYP4F3, CYP24A1, CYP2S1, CYP7B1, CYP4B1, CYP4F8, CYP26A1, CYP2U1, CYP8B1, CYP2A13, CYP4F12, CYP5A1, CYP26B1, CYP2W1, CYP11A1, CYP2B6, CYP8A1, CYP26C1, CYP3A43, CYP11B1, CYP2C8, CYP27B1, CYP4A22, CYP11B2, CYP4F11, CYP17A1, CYP2C18, CYP4F22, CYP19A1, CYP4V2, CYP21A2, CYP4×1, CYP27A1, CYP4Z1, CYP39A1, CYP2F1, CYP20A1, CYP46A1, CYP27C1, CYP51A1, CYP3A5, and CYP3A7, or any additional known CYP isoforms as well as those yet to be discovered. In one embodiment of the invention, the metabolism of a CYP2D6 bioactive drug covalently bound to a water-soluble oligomer is diverted to CYP3A4.

In the methods of the invention, the CYP2D6 bioactive drugs are covalently bound to a water-soluble oligomer. In one embodiment, the water-soluble oligomer is a PEG moiety. In another embodiment, the PEG moiety can be a small monomeric PEG such as a penta-, hexa-, hepta-, octa-, or nona-mer.

The CYP2D6 bioactive drugs for coupling to a water-soluble oligomer possess a free hydroxyl, carboxyl, thio, amino group, or the like (i.e., "handle") suitable for covalent attachment to the oligomer. In addition, the CYP2D6 bioactive drug can be modified by introduction of a reactive group, preferably by conversion of one of its existing functional groups to a functional group suitable for formation of a covalent linkage between the oligomer and the drug. Such techniques are known in the art.

The water-soluble oligomer typically comprises one or more monomers serially attached to form a chain of monomers. The oligomer can be formed from a single monomer type (i.e., is homo-oligomeric) or two or three monomer types (i.e., is co-oligomeric). Preferably, each oligomer is a co-oligomer of two monomers or, more preferably, is a homo-oligomer.

Accordingly, each oligomer is composed of up to three different monomer types selected from the group consisting of: alkylene oxide, such as ethylene oxide or propylene oxide; olefinic alcohol, such as vinyl alcohol, 1-propenol or 2-propenol; vinyl pyrrolidone; hydroxyalkyl methacrylamide or hydroxyalkyl methacrylate, where alkyl is preferably methyl; α-hydroxy acid, such as lactic acid or glycolic acid; phosphazene, oxazoline, amino acids, carbohydrates such as monosaccharides, saccharide or mannitol; and N-acryloylmorpholine. Preferred monomer types include alkylene oxide, olefinic alcohol, hydroxyalkyl methacrylamide or methacrylate, N-acryloylmorpholine, and α-hydroxy acid. Preferably, each oligomer is, independently, a co-oligomer of two monomer types selected from this group, or, more preferably, is a homo-oligomer of one monomer type selected from this group.

The two monomer types in a co-oligomer may be of the same monomer type, for example, two alkylene oxides, such as ethylene oxide and propylene oxide. Preferably, the oligomer is a homo-oligomer of ethylene oxide. Usually, although not necessarily, the terminus (or termini) of the oligomer that is not covalently attached to a CYP2D6 bioactive drug is capped to render it unreactive. Alternatively, the terminus may include a reactive group. When the terminus is a reactive group, the reactive group is either selected such that it is unreactive under the conditions of formation of the final oligomer or during covalent attachment of the oligomer to a small molecule drug, or it is protected as necessary. One common end-functional group is hydroxyl or —OH, particularly for oligoethylene oxides.

The water-soluble oligomer can have any of a number of different geometries. For example, the water-soluble oligomer can be linear, branched, or forked. Most typically, the water-soluble oligomer is linear or is branched, for example, having one branch point. Although much of the discussion herein is focused upon poly(ethylene oxide) as an illustrative oligomer, the discussion and structures presented herein can be readily extended to encompass any of the water-soluble oligomers described above.

The molecular weight of the water-soluble oligomer, excluding the linker portion, is generally relatively low. Exemplary values of the molecular weight of the water-soluble oligomer include: below about 1500; below about 1450; below about 1400; below about 1350; below about 1300; below about 1250; below about 1200; below about 1150; below about 1100; below about 1050; below about 1000; below about 950; below about 900; below about 850; below about 800; below about 750; below about 700; below about 650; below about 600; below about 550; below about 500; below about 450; below about 400; below about 350; below about 300; below about 250; below about 200; and below about 100 Daltons.

Exemplary ranges of molecular weights of the water-soluble oligomer (excluding the linker) include: from about 100 to about 1400 Daltons; from about 100 to about 1200 Daltons; from about 100 to about 800 Daltons; from about 100 to about 500 Daltons; from about 100 to about 400 Daltons; from about 200 to about 500 Daltons; from about 200 to about 400 Daltons; from about 75 to 1000 Daltons; and from about 75 to about 750 Daltons.

Preferably, the number of monomers in the water-soluble oligomer falls within one or more of the following ranges: between about 1 and about 30 (inclusive); between about 1 and about 25; between about 1 and about 20; between about 1 and about 15; between about 1 and about 12; between about 1 and about 10. In other embodiments, the number of monomers in the water-soluble oligomer falls within one or more of the following ranges: 3-13, 2-10, 3-7, 8-13, 8-10, 3-6, 3-9, 4-8, 5-8, 5-7, 3-5, 3-6, 3-7, 4-5, 4-6, 4-7, 3-4, 4-5, 5-6, 6-7, and 7-8. In certain instances, the number of monomers in series in the oligomer (and the corresponding conjugate) is one of 1, 2, 3, 4, 5, 6, 7, or 8. In additional embodiments, the oligomer (and the corresponding conjugate) contains 9, 10, 11, 12, 13, 14, 15, 16, 17, 18, 19, or 20 monomers in series. In yet further embodiments, the oligomer (and the corresponding conjugate) possesses 21, 22, 23, 24, 25, 26, 27, 28, 29 or 30 monomers in series. Thus, for example, when the water-soluble oligomer includes $CH_3$—$(OCH_2CH_2)_n$—, "n" is an integer that can be 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30, and can fall within one or more of the following ranges: between about 1 and about 25; between about 1 and about 20; between about 1 and about 15; between about 1 and about 12; between about 1 and about 10; 3-13; 2-10; 3-7; 8-13; 8-10; 3-6; 3-9; 4-8; 5-8; 5-7; 3-5; 3-6; 3-7; 4-5; 4-6; 4-7; 3-4; 4-5; 5-6; 6-7; and 7-8. In certain embodiments of the invention, the water-soluble oligomer is PEG, having the number of monomers in series or ranges of monomers as recited above.

When the water-soluble oligomer has 1, 2, 3, 4, 5, 6, 7, 8, 9, or 10 monomers, these values correspond to a methoxy end-capped oligo(ethylene oxide) having a molecular weight of about 75, 119, 163, 207, 251, 295, 339, 383, 427, and 471 Daltons, respectively. When the oligomer has 11, 12, 13, 14, or 15 monomers, these values correspond to methoxy end-capped oligo(ethylene oxide) having molecular weights corresponding to about 515, 559, 603, 647, and 691 Daltons, respectively.

When the water-soluble oligomer is attached to the CYP2D6 bioactive drug (in contrast to the step-wise addition of one or more monomers to effectively "grow" the oligomer onto the CYP2D6 bioactive drug), it is preferred that the composition containing an activated form of the water-soluble oligomer be monodispersed. In those instances, however, where a bimodal or polydispersed composition is employed, the composition will possess a bimodal distribution centering around any two of the above numbers of monomers. Ideally, the polydispersity index of each peak in the bimodal distribution, Mw/Mn, is 1.01 or less, and even more preferably, is 1.001 or less, and even more preferably is 1.0005 or less. Most preferably, each peak possesses a MW/Mn value of 1.0000. For instance, a bimodal oligomer may have any one of the following exemplary combinations of monomer subunits: 1-2, 1-3, 1-4, 1-5, 1-6, 1-7, 1-8, 1-9, 1-10, and so forth; 2-3, 2-4, 2-5, 2-6, 2-7, 2-8, 2-9, 2-10, and so forth; 3-4, 3-5, 3-6, 3-7, 3-8, 3-9, 3-10, and so forth; 4-5, 4-6, 4-7, 4-8, 4-9, 4-10, and so forth; 5-6, 5-7, 5-8, 5-9, 5-10, and so forth; 6-7, 6-8, 6-9, 6-10, and so forth; 7-8, 7-9, 7-10, and so forth; and 8-9, 8-10, and so forth.

In some instances, the composition containing an activated form of the water-soluble oligomer will be trimodal or even tetramodal, possessing a range of monomers units as previously described. Oligomer compositions possessing a well-defined mixture of oligomers (i.e., being bimodal, trimodal, tetramodal, and so forth) can be prepared by mixing purified monodisperse oligomers to obtain a desired profile of oligomers (a mixture of two oligomers differing only in the number of monomers is bimodal; a mixture of three oligomers differing only in the number of monomers is trimodal; a mixture of four oligomers differing only in the number of monomers is tetramodal), or alternatively, can be obtained from column chromatography of a polydisperse oligomer by recovering the "center cut", to obtain a mixture of oligomers in a desired and defined molecular weight range.

It is preferred that the water-soluble oligomer is obtained from a composition that is preferably unimolecular or monodisperse. That is, the oligomers in the composition possess the same discrete molecular weight value rather than a distribution of molecular weights. Some monodisperse oligomers can be purchased from commercial sources such as those available from Sigma-Aldrich, or alternatively, can be prepared directly from commercially available starting materials available from commercial suppliers such as Sigma-Aldrich. Water-soluble oligomers can be prepared as described in Chen Y., Baker, G. L., J. Org. Chem., 6870-6873 (1999), WO 02/098949, and U.S. Patent Application Publication 2005/0136031.

The spacer moiety (through which the water-soluble and oligomer is attached to the CYP2D6 bioactive drug) may be a covalent bond, a single atom, such as an oxygen or a sulfur, two atoms, or a number of atoms. A spacer moiety is typically but is not necessarily linear in nature. The spacer moiety, "X" can be hydrolytically stable in some instances and can be degradable when, for example, a prodrug approach is desired. The linkage is preferably also enzymatically stable. Preferably, the spacer moiety "X" is one having a chain length of less than about 12 atoms, and preferably less than about 10 atoms, and even more preferably less than about 8 atoms and even more preferably less than about 5 atoms, whereby length is meant the number of atoms in a single chain, not counting substituents. For instance, a urea linkage such as this, $R_{oligomer}$—NH—(C=O)—NH—$R'_{drug}$, is considered to have a chain length of 3 atoms (—NH—C(O)—NH—). In selected embodiments, the linkage does not comprise further spacer groups.

In some instances, the spacer moiety "X" comprises an ether, amide, urethane, amine, thioether, urea, or a carbon-carbon bond. Functional groups such as those discussed below, and illustrated in the examples, are typically used for forming the spacer moieties. The spacer moiety may less preferably also comprise (or be adjacent to or flanked by) spacer groups, as described further below. Spacers are most useful in instances where the bioactivity of the conjugate is significantly reduced due to the positioning of the oligomer on the parent drug.

More specifically, in selected embodiments, a spacer moiety of the invention, X, may be any of the following: "—" (i.e., a covalent bond, that may be stable or degradable, between the residue of the CYP2D6 bioactive drug and the water-soluble oligomer), —O—, —NH—, —S—, —C(O)—, C(O)—NH, NH—C(O)—NH, O—C(O)—NH, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—C(O)—NH—CH$_2$—CH$_2$—, —CH$_2$—CH$_2$—C(O)—NH—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$—, —CH$_2$—CH$_2$—NH—C(O)—CH$_2$—CH$_2$—, —C(O)—NH—CH$_2$—, —C(O)—NH—CH$_2$—CH$_2$—, —O—C(O)—NH—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, bivalent cycloalkyl group, —N(R$^6$)—, R$^6$ is H or an organic radical selected from the group consisting of alkyl, substituted alkyl, alkenyl, substituted alkenyl, alkynyl, substituted alkynyl, aryl and substituted aryl.

For purposes of the present invention, however, a series of atoms is not considered as a spacer moiety when the series of atoms is immediately adjacent to an oligomer segment, and the series of atoms is but another monomer such that the proposed spacer moiety would represent a mere extension of the oligomer chain.

The spacer moiety "X" between the water-soluble oligomer and the small molecule is typically formed by reaction of a functional group on a terminus of the oligomer (or one or more monomers when it is desired to "grow" the oligomer onto the CYP2D6 bioactive drug) with a corresponding functional group within the CYP2D6 bioactive drug. Illustrative reactions are described briefly below. For example, an amino group on an oligomer may be reacted with a carboxylic acid or an activated carboxylic acid derivative on the small molecule, or vice versa, to produce an amide linkage. Alternatively, reaction of an amine on an oligomer with an activated carbonate (e.g. succinimidyl or benzotriazyl carbonate) on the drug, or vice versa, forms a carbamate linkage. Reaction of an amine on an oligomer with an isocyanate (R—N=C=O) on a drug, or vice versa, forms a urea linkage (R—NH—(C=O)—NH—R'). Further, reaction of an alcohol (alkoxide) group on an oligomer with an alkyl halide, or halide group within a drug, or vice versa, forms an ether linkage. In yet another coupling approach, a small molecule having an aldehyde group is coupled to an oligomer amino group by reductive amination, resulting in formation of a secondary amine linkage between the oligomer and the small molecule.

A particularly preferred water-soluble oligomer is an oligomer bearing an aldehyde functional group. In this regard, the oligomer will have the following structure: $CH_3O-(CH_2-CH_2-O)_n-(CH_2)_p-C(O)H$, wherein (n) is one of 1, 2, 3, 4, 5, 6, 7, 8, 9 and 10 and (p) is one of 1, 2, 3, 4, 5, 6 and 7. Preferred (n) values include 3, 5 and 7 and preferred (p) values 2, 3 and 4. In addition, the carbon atom alpha to the —C(O)H moiety can optionally be substituted with alkyl.

Typically, the terminus of the water-soluble oligomer not bearing a functional group is capped to render it unreactive. When the oligomer does includes a further functional group at a terminus other than that intended for formation of a conjugate, that group is either selected such that it is unreactive under the conditions of formation of the spacer moiety "X," or it is protected during the formation of the spacer moiety "X."

As stated above, the water-soluble oligomer includes at least one functional group prior to conjugation. The functional group typically comprises an electrophilic or nucleophilic group for covalent attachment to a small molecule, depending upon the reactive group contained within or introduced into the small molecule. Examples of nucleophilic groups that may be present in either the oligomer or the small molecule include hydroxyl, amine, hydrazine (—NHNH$_2$), hydrazide (—C(O)NHNH$_2$), and thiol. Preferred nucleophiles include amine, hydrazine, hydrazide, and thiol, particularly amine. Most small molecule drugs for covalent attachment to an oligomer will possess a free hydroxyl, amino, thio, aldehyde, ketone, or carboxyl group.

Examples of electrophilic functional groups that may be present in either the oligomer or the small molecule include carboxylic acid, carboxylic ester, particularly imide esters, orthoester, carbonate, isocyanate, isothiocyanate, aldehyde, ketone, thione, alkenyl, acrylate, methacrylate, acrylamide, sulfone, maleimide, disulfide, iodo, epoxy, sulfonate, thiosulfonate, silane, alkoxysilane, and halosilane. More specific examples of these groups include succinimidyl ester or carbonate, imidazoyl ester or carbonate, benzotriazole ester or carbonate, vinyl sulfone, chloroethylsulfone, vinylpyridine, pyridyl disulfide, iodoacetamide, glyoxal, dione, mesylate, tosylate, and tresylate (2,2,2-trifluoroethanesulfonate).

Also included are sulfur analogs of several of these groups, such as thione, thione hydrate, thioketal, is 2-thiazolidine thione, etc., as well as hydrates or protected derivatives of any of the above moieties (e.g. aldehyde hydrate, hemiacetal, acetal, ketone hydrate, hemiketal, ketal, thioketal, thioacetal).

An "activated derivative" of a carboxylic acid refers to a carboxylic acid derivative which reacts readily with nucleophiles, generally much more readily than the underivatized carboxylic acid. Activated carboxylic acids include, for example, acid halides (such as acid chlorides), anhydrides, carbonates, and esters. Such esters include imide esters, of the general form —(CO)O—N[(CO)—]$_2$; for example, N-hydroxysuccinimidyl (NHS) esters or N-hydroxyphthalimidyl esters. Also preferred are imidazolyl esters and benzotriazole esters. Particularly preferred are activated propionic acid or butanoic acid esters, as described in co-owned U.S. Pat. No. 5,672,662. These include groups of the form —(CH$_2$)$_{2-3}$C(=O)O-Q, where Q is preferably selected from N-succinimide, N-sulfosuccinimide, N-phthalimide, N-glutarimide, N-tetrahydrophthalimide, N-norbornene-2,3-dicarboximide, benzotriazole, 7-azabenzotriazole, and imidazole.

Other preferred electrophilic groups include succinimidyl carbonate, maleimide, benzotriazole carbonate, glycidyl ether, imidazoyl carbonate, p-nitrophenyl carbonate, acrylate, tresylate, aldehyde, and orthopyridyl disulfide.

These electrophilic groups are subject to reaction with nucleophiles, e.g. hydroxy, thio, or amino groups, to produce various bond types. Preferred for the present invention are reactions which favor formation of a hydrolytically stable linkage. For example, carboxylic acids and activated derivatives thereof, which include orthoesters, succinimidyl esters, imidazolyl esters, and benzotriazole esters, react with the above types of nucleophiles to form esters, thioesters, and amides, respectively, of which amides are the most hydrolytically stable. As mentioned above, most preferred are conjugates having a hydrolytically stable linkage between the oligomer and the drug. Carbonates, including succinimidyl, imidazolyl, and benzotriazole carbonates, react with amino groups to form carbamates. Isocyanates (R—N=C=O) react with hydroxyl or amino groups to form, respectively, carbamate (RNH—C(O)—OR') or urea (RNH—C(O)—NHR') linkages. Aldehydes, ketones, glyoxals, diones and their hydrates or alcohol adducts (i.e., aldehyde hydrate, hemiacetal, acetal, ketone hydrate, hemiketal, and ketal) are preferably reacted with amines, followed by reduction of the resulting imine, if desired, to provide an amine linkage (reductive amination).

Several of the electrophilic functional groups include electrophilic double bonds to which nucleophilic groups, such as thiols, can be added, to form, for example, thioether bonds. These groups include maleimides, vinyl sulfones, vinyl pyridine, acrylates, methacrylates, and acrylamides. Other groups comprise leaving groups which can be displaced by a nucleophile; these include chloroethyl sulfone, pyridyl disulfides (which include a cleavable S—S bond), iodoacetamide, mesylate, tosylate, thiosulfonate, and tresylate. Epoxides react by ring opening by a nucleophile, to form, for example, an ether or amine bond. Reactions involving complementary reactive groups such as those noted above on the oligomer and the small molecule are utilized to prepare the conjugates of the invention.

In some instances the CYP2D6 bioactive drug may not have a functional group suited for conjugation. In this instance, it is possible to modify the "original" CYP2D6 bioactive drug so that it does have a functional group suited for conjugation. For example, if the CYP2D6 bioactive drug has an amide group, but an amine group is desired, it is possible to modify the amide group to an amine group by way of a Hofmann rearrangement, Curtius rearrangement (once the amide is converted to an azide) or Lossen rearrangement (once amide is concerted to hydroxamide followed by treatment with tolyene-2-sulfonyl chloride/base).

It is possible to prepare a conjugate of a CYP2D6 bioactive drug bearing a carboxyl group wherein the carboxyl group-bearing CYP2D6 bioactive drug is coupled to an amino-terminated oligomeric ethylene glycol, to provide a conjugate having an amide group covalently linking the CYP2D6 bioactive drug to the oligomer. This can be performed, for example, by combining the carboxyl group-bearing CYP2D6 bioactive drug with the amino-terminated oligomeric ethylene glycol in the presence of a coupling reagent, (such as dicyclohexylcarbodiimide or "DCC") in an anhydrous organic solvent.

Further, it is possible to prepare a conjugate of a CYP2D6 bioactive drug bearing a hydroxyl group wherein the hydroxyl group-bearing CYP2D6 bioactive drug is coupled to an oligomeric ethylene glycol halide to result in an ether (—O—) linked small molecule conjugate. This can be performed, for example, by using sodium hydride to deprotonate the hydroxyl group followed by reaction with a halide-terminated oligomeric ethylene glycol.

In another example, it is possible to prepare a conjugate of a CYP2D6 bioactive drug bearing a ketone group by first reducing the ketone group to form the corresponding hydroxyl group. Thereafter, the CYP2D6 bioactive drug now bearing a hydroxyl group can be coupled as described herein.

In still another instance, it is possible to prepare a conjugate of a CYP2D6 bioactive drug bearing an amine group. In one approach, the amine group-bearing CYP2D6 bioactive drug and an aldehyde-bearing oligomer are dissolved in a suitable buffer after which a suitable reducing agent (e.g., $NaCNBH_3$) is added. Following reduction, the result is an amine linkage formed between the amine group of the amine group-containing CYP2D6 bioactive drug and the carbonyl carbon of the aldehyde-bearing oligomer.

In another approach for preparing a conjugate of a CYP2D6 bioactive drug bearing an amine group, a carboxylic acid-bearing oligomer and the amine group-bearing CYP2D6 bioactive drug are combined, typically in the presence of a coupling reagent (e.g., DCC). The result is an amide linkage formed between the amine group of the amine group-containing CYP2D6 bioactive drug and the carbonyl of the carboxylic acid-bearing oligomer.

The conjugates used in the methods of the invention exhibit reduced metabolism by or affinity to CYP2D6. In some cases, the reduction in metabolism by CYP2D6 in vivo or in vitro is by at least 95%, at least 90%, at least 85%, at least 80%, at least 75%, at least 70%, at least 65%, at least 60%, at least 55%, at least 50%, at least 45%, at least 40%, at least 35%, at least 30%, at least 25%, at least 20%, at least 15%, at least 10%, or at least 5%. In one preferred embodiment, the reduction in metabolism by CYP2D6 is at least 50%, in other preferred embodiments, the reduction is at least 40% or is at least 30%.

The selection of an optimally sized oligomer can be determined through routine experimentation.

CYP2D6 bioactive drug conjugates may be administered according to the methods of the invention in the form of pharmaceutical preparations comprising a conjugate as provided herein in combination with a pharmaceutical excipient. Generally, the conjugate itself will be in a solid form (e.g., a precipitate), which can be combined with a suitable pharmaceutical excipient that can be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myo-inositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the conjugate in the composition will vary depending on a number of factors, but will optimally be a therapeutically effective dose when the composition is stored in a unit dose container. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5%-98% by weight, more preferably from about 15-95% by weight of the excipient, with concentrations less than 30% by weight most preferred.

These foregoing pharmaceutical excipients along with other excipients are described in "Remington: The Science & Practice of Pharmacy", $19^{th}$ ed., Williams & Williams, (1995), the "Physician's Desk Reference", $52^{nd}$ ed., Medical Economics, Montvale, N.J. (1998), and Kibbe, A. H., Handbook of Pharmaceutical Excipients, $3^{rd}$ Edition, American Pharmaceutical Association, Washington, D.C., 2000.

The pharmaceutical compositions can take any number of forms and the invention is not limited in this regard. Exemplary preparations are most preferably in a form suitable for oral administration such as a tablet, caplet, capsule, gel cap, troche, dispersion, suspension, solution, elixir, syrup, lozenge, transdermal patch, spray, suppository, and powder.

Oral dosage forms are preferred for those conjugates that are orally active, and include tablets, caplets, capsules, gel caps, suspensions, solutions, elixirs, and syrups, and can also comprise a plurality of granules, beads, powders or pellets that are optionally encapsulated. Such dosage forms are prepared using conventional methods known to those in the field of pharmaceutical formulation and described in the pertinent texts.

Tablets and caplets, for example, can be manufactured using standard tablet processing procedures and equipment. Direct compression and granulation techniques are preferred when preparing tablets or caplets containing the conjugates described herein. In addition to the conjugate, the tablets and caplets will generally contain inactive, pharmaceutically acceptable carrier materials such as binders, lubricants, disintegrants, fillers, stabilizers, surfactants, coloring agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

Capsules are also preferred oral dosage forms, in which case the conjugate-containing composition can be encapsulated in the form of a liquid or gel (e.g., in the case of a gel cap) or solid (including particulates such as granules, beads, powders or pellets). Suitable capsules include hard and soft capsules, and are generally made of gelatin, starch, or a cellulosic material. Two-piece hard gelatin capsules are preferably sealed, such as with gelatin bands or the like.

Included are parenteral formulations in the substantially dry form (typically as a lyophilizate or precipitate, which can be in the form of a powder or cake), as well as formulations prepared for injection, which are typically liquid and requires the step of reconstituting the dry form of parenteral formulation. Examples of suitable diluents for reconstituting solid compositions prior to injection include bacteriostatic water for injection, dextrose 5% in water, phosphate-buffered saline, Ringer's solution, saline, sterile water, deionized water, and combinations thereof.

In some cases, compositions intended for parenteral administration can take the form of nonaqueous solutions, suspensions, or emulsions, each typically being sterile. Examples of nonaqueous solvents or vehicles are propylene glycol, polyethylene glycol, vegetable oils, such as olive oil and corn oil, gelatin, and injectable organic esters such as ethyl oleate.

The parenteral formulations described herein can also contain adjuvants such as preserving, wetting, emulsifying, and dispersing agents. The formulations are rendered sterile by incorporation of a sterilizing agent, filtration through a bacteria-retaining filter, irradiation, or heat.

The conjugate can also be administered through the skin using conventional transdermal patch or other transdermal delivery system, wherein the conjugate is contained within a laminated structure that serves as a drug delivery device to be affixed to the skin. In such a structure, the conjugate is contained in a layer, or "reservoir," underlying an upper backing layer. The laminated structure can contain a single reservoir, or it can contain multiple reservoirs.

The conjugate can also be formulated into a suppository for rectal administration. With respect to suppositories, the conjugate is mixed with a suppository base material which is (e.g., an excipient that remains solid at room temperature but softens, melts or dissolves at body temperature) such as coca butter (theobroma oil), polyethylene glycols, glycerinated gelatin, fatty acids, and combinations thereof. Suppositories can be prepared by, for example, performing the following steps (not necessarily in the order presented): melting the suppository base material to form a melt; incorporating the conjugate (either before or after melting of the suppository base material); pouring the melt into a mold; cooling the melt (e.g., placing the melt-containing mold in a room temperature environment) to thereby form suppositories; and removing the suppositories from the mold.

The CYP2D6 bioactive drug conjugates are administered generally orally, in a therapeutically effective amount (preferably provided as part of a pharmaceutical preparation). Other modes of administration are also contemplated, such as pulmonary, nasal, buccal, rectal, sublingual, transdermal, and parenteral. As used herein, the term "parenteral" includes subcutaneous, intravenous, intra-arterial, intraperitoneal, intracardiac, intrathecal, and intramuscular injection, as well as infusion injections.

In instances where parenteral administration is utilized, it may be necessary to employ somewhat bigger oligomers than those described previously, with molecular weights ranging from about 500 to 30K Daltons (e.g., having molecular weights of about 500, 1000, 2000, 2500, 3000, 5000, 7500, 10000, 15000, 20000, 25000, 30000 or even more).

Those of ordinary skill in the art appreciate which conditions a specific conjugate can effectively treat. The actual dose to be administered will vary depend upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 1000 mg, preferably in doses from 0.01 mg/day to 750 mg/day, and more preferably in doses from 0.10 mg/day to 500 mg/day.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

In a further embodiment, the invention provides a method of identifying a candidate compound for administration to a CYP2D6 alternative metabolizer comprising assaying for the extent of metabolism of a test compound by CYP2D6; assaying for the extent of metabolism of the test compound covalently bound to a water-soluble oligomer, by CYP2D6; and identifying a test compound as a candidate compound as one for which the degree of metabolism by CYP2D6 is less for the test compound covalently bound to a water-soluble oligomer than the test compound without the covalently bound water-soluble oligomer. Preferably, the water-soluble oligomer is a PEG moiety. Assaying for the extent of metabolism may be achieved by any method known in the art, including those discussed previously.

In another embodiment, the invention provides a compound comprising the formula D-X-POLY, wherein POLY is a water-soluble oligomer, preferably a polyethylene glycol (PEG) moiety, X is spacer moiety, and D is a CYP2D6 bioactive drug, preferably a small molecule drug. In some instances, it is preferred that the CYP2D6 bioactive drug, D, is not a nucleotide, nucleoside, antihistamine, oxymorphone, platinum coordination complex based drug, steroid, fluoroquinolone, retinoid, phenothiazine, benzodiazepine, galactogugues, thiazide, amlodipine, nifedipine, nimodipine, 5-hydroxytryptophan, nevirapine, amifostine, amiodarone, aminocaproic acid, aminohippurate sodium, aminoglutethimide, aminolevulinic acid, aminosalicylic acid, amsacrine, anagrelide, anastrozole, asparaginase, anthracyclines, bexarotene, bicalutamide, bleomycin, buserelin, busulfan, cabergoline, capecitabine, carboplatin, carmustine, chlorambucil, cilastatin sodium, cladribine, clodronate, cyclophosphamide, cyproterone, cytarabine, camptothecins, dacarbazine, dactinomycin, daunorubicin, deferoxamine, diclofenac, docetaxel, doxorubicin, epirubicin, estramustine, etoposide, exemestane, fexofenadine, fludarabine, flu- oxymesterone, flutamide, gemcitabine, epinephrine, L-Dopa, hydroxyurea, idarubicin, ifosfamide, imatinib, irinotecan, itraconazole, goserelin, letrozole, leucovorin, levamisole, lisinopril, lovothyroxine sodium, lomustine, mechlorethamine, melphalan, mercaptopurine, metaraminol bitartrate, methotrexate, metoclopramide, mexiletine, mitomycin, mitotane, mitoxantrone, nicotine, nilutamide, octreotide, pamidronate, pentostatin, pilcamycin, porfimer, procarbazine, prochlorperazine, ondansetron, raltitrexed, sirolimus, streptozocin, tacrolimus, tamoxifen, temozolomide, teniposide, tetrahydrocannabinol, thalidomide, thiotepa, topotecan, tretinoin, valrubicin, vinblastine, vincristine, vindesine, vinorelbine, dolasetron, granisetron; formoterol, leuprolide, amphotericin B, podophylotoxins, nucleoside antivirals, aroyl hydrazones or sumatriptan. In some embodiments, it is preferred that the CYP2D6 bioactive drug is one of the foregoing.

EXAMPLES

It is to be understood that while the invention has been described in conjunction with certain preferred and specific embodiments, the foregoing description as well as the examples that follow are intended to illustrate and not limit the scope of the invention. Other aspects, advantages and modifications within the scope of the invention will be apparent to those skilled in the art to which the invention pertains.

All chemical reagents referred to in the appended examples are commercially available unless otherwise indicated. The preparation of PEG-mers is described in, for example, U.S. Patent Application Publication No. 2005/0136031.

Example 1

PEG-Diphenhydramine Conjugates Exhibit a Shift in Affinity from CYP2D6 to CYP3A4, Whereas Diphenhydramine Interacts Only with CYP2D6

The affinity of diphenhydramine for 2D6 was found to be characterized by an $IC_{50}$ of 7.6 µM, as determined by inhibition of metabolism of the classical high-affinity 2D6 substrate bufuralol (FIG. 1).

Conjugation of small PEG molecules containing 5, 6 or 7 ethylene glycol units to diphenhydramine yielded novel molecules termed PEG-5-diphenhydramine (PEG-5-DPH), PEG-6-diphenhydramine (PEG-6-DPH) and PEG-7-diphenhydramine (PEG-7-DPH) respectively. Briefly, benzhydryl 2-chloroethyl ether (2 mmol) and mPEG$_n$-NH$_2$ (3 mmol) were dissolved in 10 ml of acetonitrile, and then sodium hydroxide (2 mmol) in water (1 mL) was added to the solution. The mixture was stirred at 100° C. for 16 hours. Dichloromethane (200 ml) was added to the reaction mixture, and the resulting solution was washed with water (200 mL×3). The organic phase was dried and solvent was removed under reduced pressure. The crude product was purified to yield the desired PEG-n-DPH conjugate. Microsomal inhibition studies using bufuralol demonstrated that PEG conjugation led to a decrease in affinity for CYP2D6. Thus $IC_{50}$ values for PEG-5-DPH, PEG-6-DPH and PEG-7-DPH were 25.3 µM, 17.3 µM and 27.0 µM respectively (FIG. 1).

Figure 2:
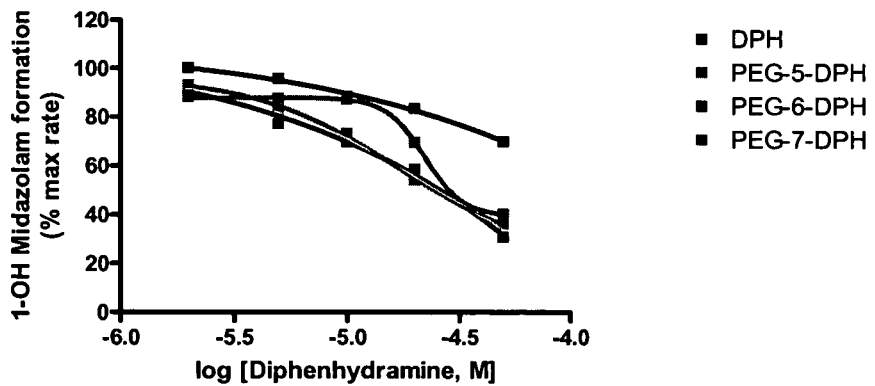
FIG. 2 shows the inhibition of CYP3A4 metabolism by diphenhydramine (DPH) and PEG-DPH. PEG conjugates interacted with CYP3A4 whereas unconjugated DPH did not.

In contrast to the behavior seen using CYP2D6, diphenhydramine was not found to interact with CYP3A4, using similar inhibition studies with the high affinity CYP3A4 substrate midazolam. All three PEG-DPH molecules, however, demonstrated significant interaction with CYP3A4, characterized by $IC_{50}$ values of 28.3 µM, 25.7 µM and 27.5 µM (FIG. 2). The $IC_{50}$ values are summarized in Table 1.

TABLE 1

|  | 2D6 Affinity ($IC_{50}$) | 3A4 Affinity ($IC_{50}$) |
|---|---|---|
| DPH | 7.6 µM | n/a |
| PEG-5-DPH | 25.3 µM | 28.3 µM |
| PEG-6-DPH | 17.3 µM | 25.7 µM |
| PEG-7-DPH | 27.0 µM | 27.5 µM |

Thus PEG-Diphenhydramine conjugates exhibit similar or equal affinity to CYP3A4 and CYP2D6, whereas diphenhydramine interacts only with CYP2D6.

Figure 3:
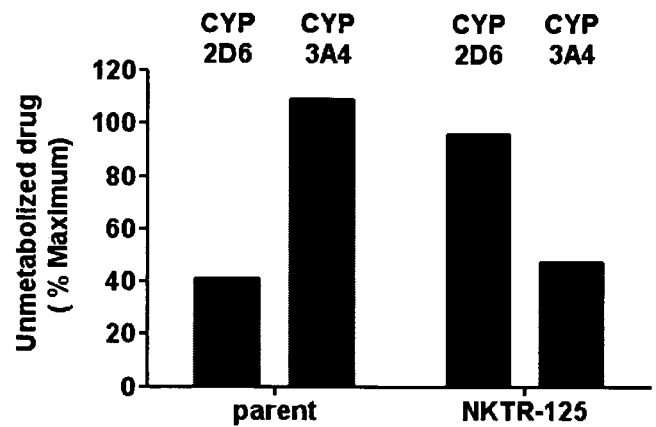
FIG. 3 shows that PEG conjugation switches metabolism of DPH from CYP2D6 to CYP3A4.

Further studies in isolated Bactosomes™ expressing recombinant CYP2D6 or CYP3A4 demonstrated clearly the altered affinity for the metabolic enzymes (FIG. 3). In this system, microsomes expressing only the indicated CYP450 isozyme were incubated with the test compound under appropriate metabolizing conditions, and the rate of disappearance of the parent compound was measured over time. Initial rates of metabolism were determined after 15 minutes incubation, and demonstrated that in the presence of CYP3A4, DPH remains completely intact and unmetabolized, whereas PEG-DPH has undergone significant metabolic conversion with only 47% of the parent PEG-DPH remaining. In the presence of CYP2D6 by contrast, 59% of DPH has been metabolized (41% unmetabolized parent remaining), while 96% of the PEG-DPH remains intact.

Figure 4:
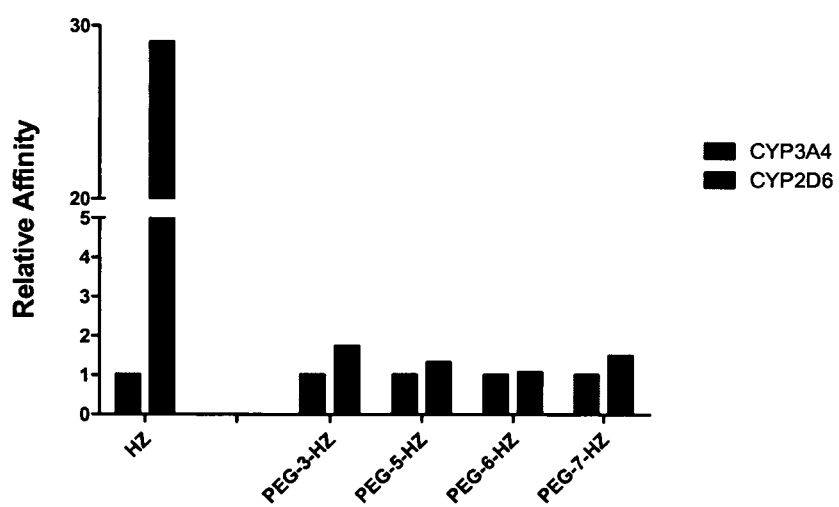
FIG. 4 shows that PEG conjugation of hydroxyzine reduces its affinity for CYP2D6 while increasing its affinity for CYP3A4.
Figure 5A:
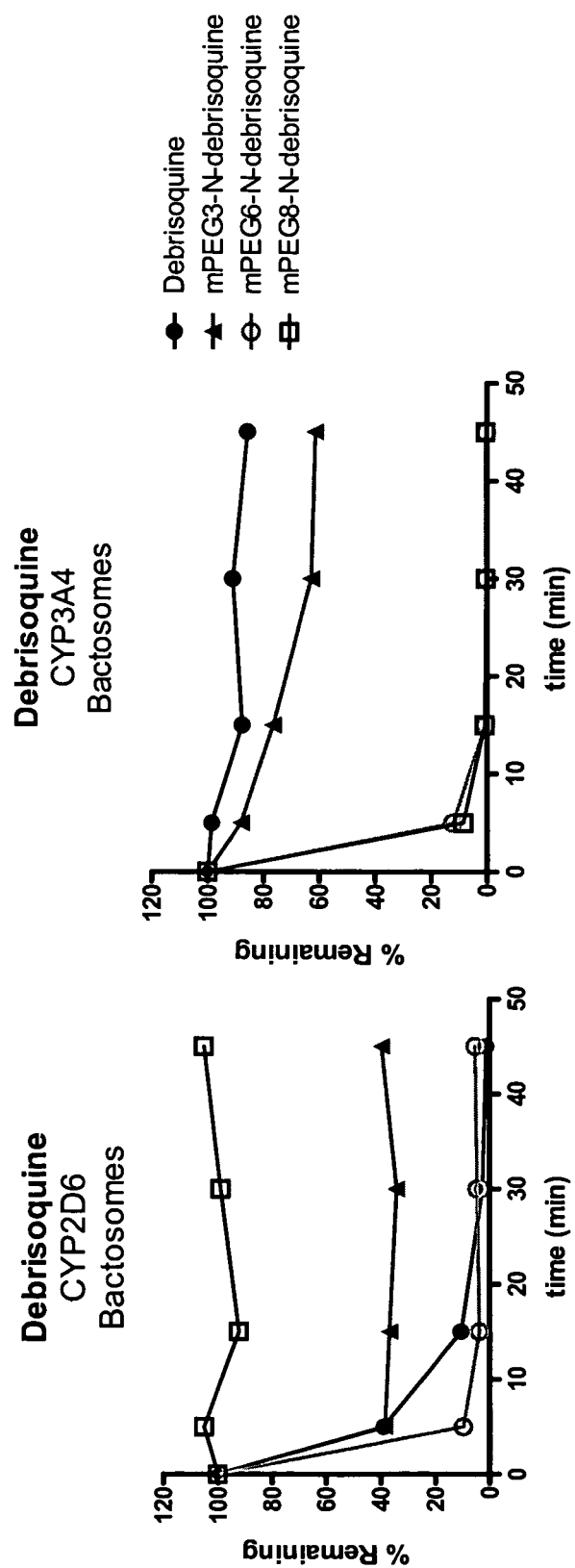
FIG. 5 shows the results of in vitro assays for CYP2D6 and CYP3A4 metabolism by (A) debrisoquine, (B) propranolol, (C) timolol, (D) hydroxyzine, (E) diphenhydramine, (F) desipramine (secondary amine conjugate), and (G) desipramine (tertiary amine conjugate).
Figure 5B:
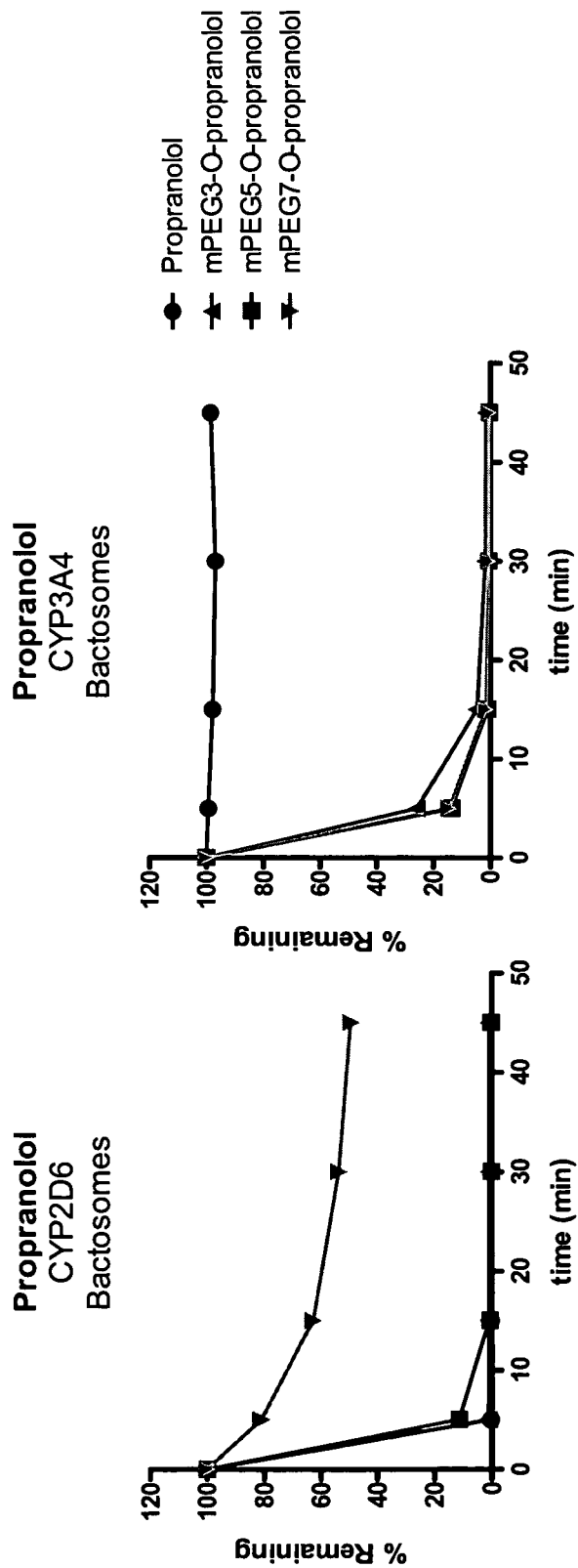
Figure 5C:
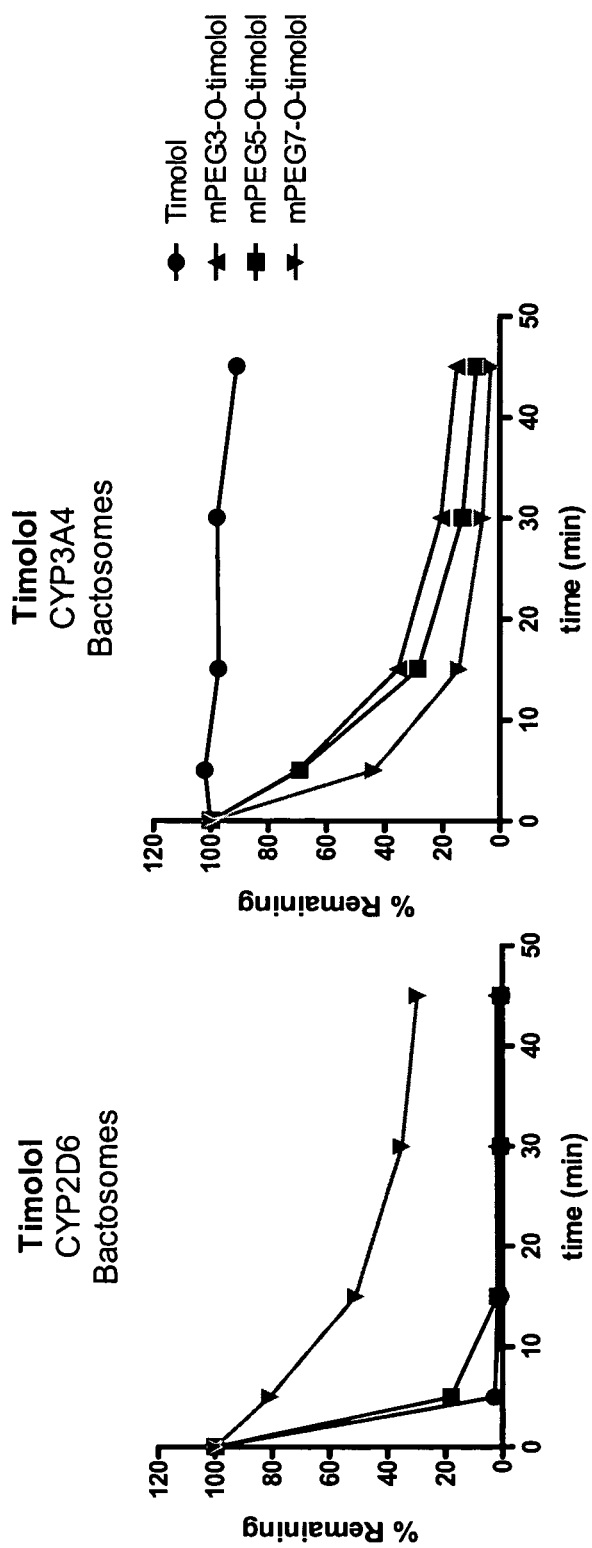
Figure 5D:
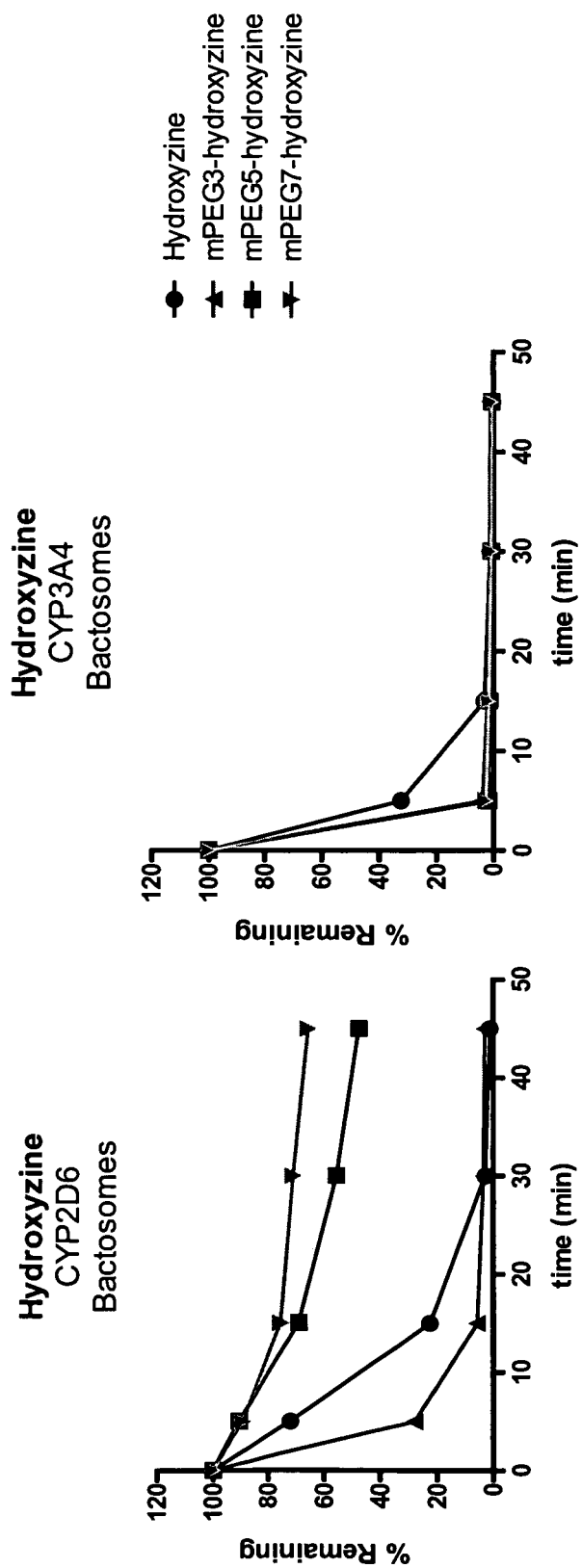
Figure 5E:
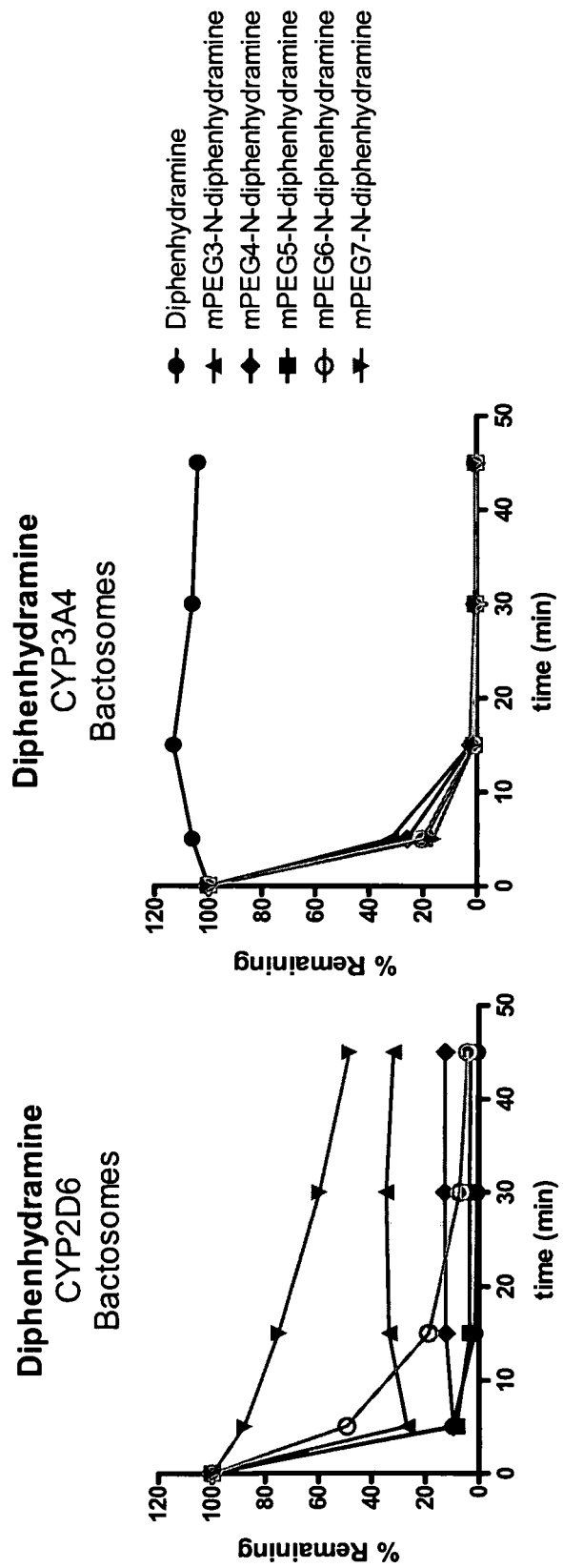
Figure 5F:
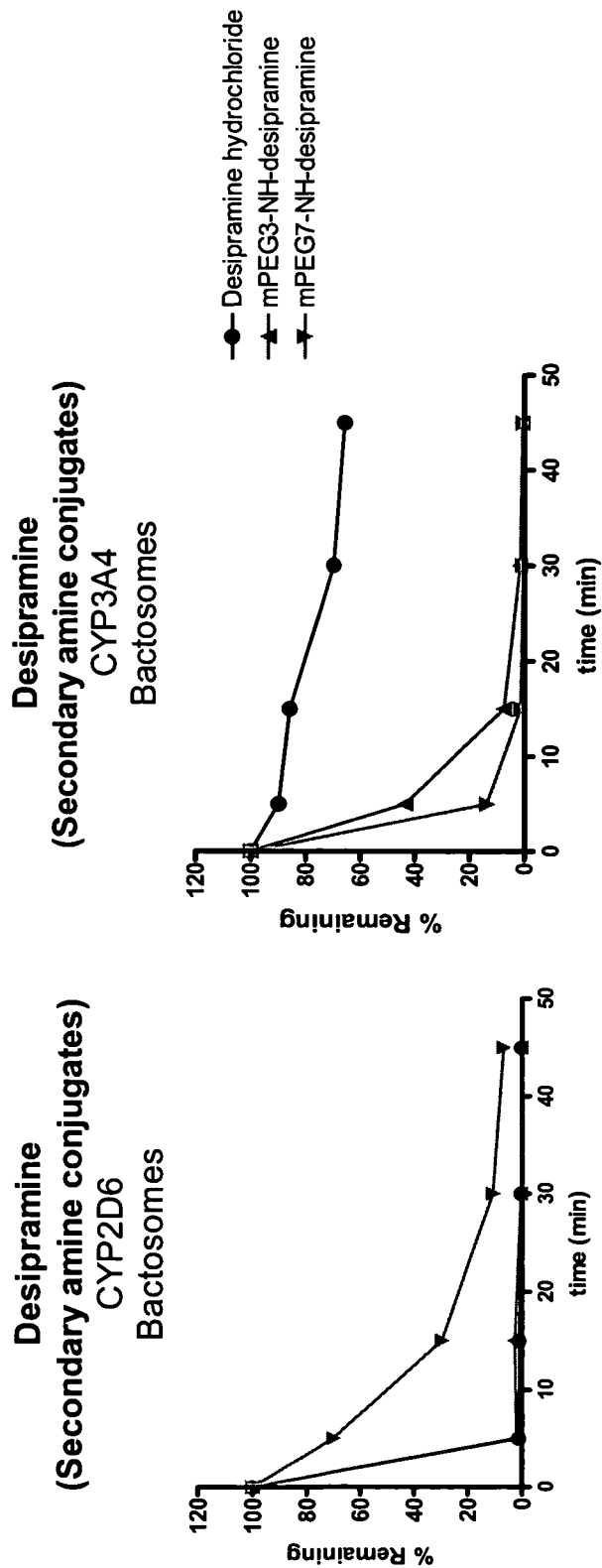
Figure 5G:
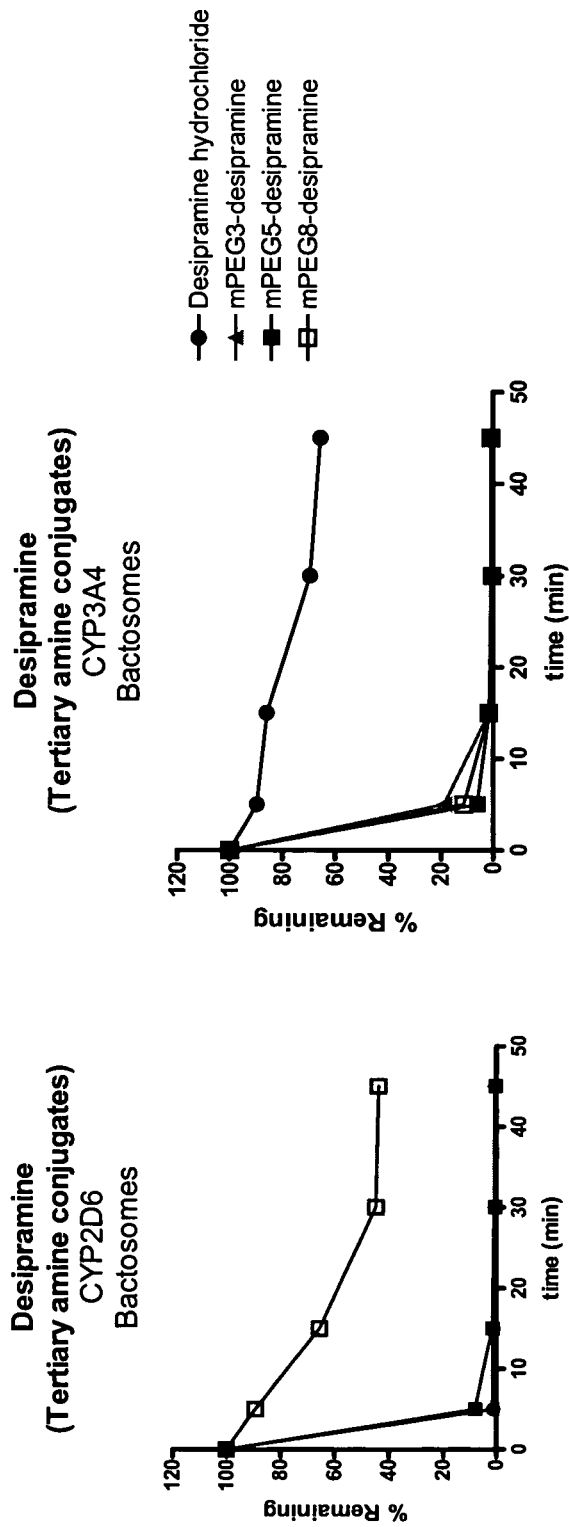

A similar effect is seen with the CYP2D6 substrate hydroxyzine (HZ). Briefly, conjugates of hydroxyzine were prepared by dissolving hydroxyzine dihydrochloride in a suitable solvent (e.g., DMF), after which to the solution, NaH (5.0 mmol) was added with stirring. After 20 minutes, mPEGn-Br (3.0 mmol) was added to the solution, which was then stirred overnight at room temperature. Dichloromethane (150 mL) was added and the precipitated solid was collected by filtration. The organic filtrate was washed with water (100 mL×2) and then dried and subsequently purified. Microsomal inhibition studies were performed on HZ and PEGylated hydroxyzine conjugates, using metabolism of bufuralol or midazolam to measure affinity for CYP2D6 or CYP3A4 respectively. Again, conjugation of small PEGs in the size range 3 to 7 ethylene glycol units (PEG-3-HZ to PEG-7-HZ) resulted in a dramatic shift in the relative affinity for the two metabolizing enzymes, as demonstrated in FIG. 4. Whereas unmodified HZ exhibited a 30-fold greater affinity for CYP2D6 than CYP3A4 (Ki—1.8 µM (2D6) vs Ki—52.3 nM (3A4)), the PEG-HZ derivatives demonstrated dramatic relative reduction in the 2D6 affinity, with approximately equal Ki values at the two enzymes. Table 2 demonstrates that for all four PEG-HZ conjugates, PEG reduces the affinity for CYP2D6 (reflected in higher $IC_{50}$ values) while increasing the affinity for CYP3A4 (reflected in lower $IC_{50}$ values).

TABLE 2

|  | 3A4 Affinity ($IC_{50}$) | 2D6 Affinity ($IC_{50}$) |
|---|---|---|
| HZ | 52.3 µM | 1.8 µM |
| PEG-3-HZ | 17.8 µM | 10.3 µM |
| PEG-5-HZ | 15.4 µM | 11.7 µM |

TABLE 2-continued

|  | 3A4 Affinity ($IC_{50}$) | 2D6 Affinity ($IC_{50}$) |
|---|---|---|
| PEG-6-HZ | 23.7 µM | 22.2 µM |
| PEG-7-HZ | 34.0 µM | 22.9 µM |

These studies demonstrate, therefore, that diphenhydramine is metabolized by CYP2D6 with no discernible metabolism by CYP3A4. In contrast, PEG-DPH conjugates exhibit a decreased affinity for CYP2D6 and a significant affinity for CYP3A4. Similarly, these experiments demonstrate a dramatic reduction in affinity of hydroxazine for CYP2D6 with a significant increase in the relative affinity for CYP3A4.

Example 2

PEG Conjugation Causes a Decrease in the Metabolism of Test Compounds by CYP2D6 and a Concomitant Increase in Metabolism by CYP3A4 In Vitro The metabolism of test compounds by specific P450 isoforms was examined by using a singly-expressed P450 isoform in *E. coli* (CYP2D6 or CYP3A4 Bactosomes™). No cell-penetration of test compounds was required in this assay system.

Timecourse analyses of test molecules (5 µM) with CYP2D6- or CYP3A4-expressing Bactosomes™ (100 pmol/mL) are performed in buffer (0.1 M phosphate, pH 7.4) in a final reaction volume of 25 µL. Samples are preincubated at 37° C., and each reaction is initiated by the addition of NADPH (1 mM final concentration). The final concentration of organic solvent is maintained at 0.25%. Reactions are terminated by the addition of methanol (50 µL) containing internal standard at 0, 5, 15, 30, and 45 minutes. Samples are centrifuged at 2500 rpm for 20 minutes at 4° C. to precipitate protein, and the supernatant is analyzed by liquid chromatography-tandem mass spectrometry.

Results of these experiments demonstrate that PEGylation of test compounds switches their metabolism from CYP2D6 to CYP3A4. See FIGS. 5A-G. All the parent compounds except hydroxyzine were stable in the presence of CYP3A4 Bactosomes™ but were extensively metabolized by the CYP2D6 Bactosomes™; the PEGylated compounds were metabolized by both isoforms or just CYP3A4 to varying degrees.

More specifically, the CYP2D6 results show persistence (high % remaining) of larger PEG sizes and rapid disappearance of parent and smaller PEG conjugates. The CYP3A4 results demonstrate a more rapid disappearance of larger PEG conjugates (low % remaining) compared with persistence of parent and smaller PEG conjugates. Particularly significant results are seen within the first five minutes of incubation, the time frame of primary significance in drug metabolism. (Voet, D. J. and Voet, J. G. 1990 Biochemistry. 1st Edition. New York: John Wiley & Sons, Inc. p 337).

Thus, PEG conjugation causes a decrease in the degree of metabolism by CYP2D6 that is PEG size-dependent and a concomitant increase in the degree of metabolism of CYP3A4 that is PEG size-dependent.

Example 3

PEG Conjugation Causes a Decrease in the Inhibitory Effects of Test Compounds on CYP2D6 and a Concomitant Increase in Inhibition of CYP3A4

As assessment of binding affinity is indicative of the probability of drug-drug interactions, microsomal inhibition assays were conducted to assess the competitive inhibition of binding to the CYP2D6 and CYP3A4 isoforms by inhibiting metabolic conversion of standard marker compounds. The metabolism of the fixed concentration of a probe substrate (dextromethorphan for CYP2D6; midazolam or testosterone for CYP3A4) was inhibited by coincubated test compounds at the test compound concentrations of 0, 0.1, 0.25, 1, 2.5, 10, and 25 µM. The degree of inhibition was displayed as $IC_{50}$. The assay was using cell-free system-human liver microsomes as a source of human P450s.

Inhibition studies are performed by incubating multiple concentrations of test compound (0.1-25 µM) with individual CYP isoform-specific probe substrates in buffer (0.1 M phosphate buffer, pH 7.4) containing human liver microsomes (0.1 mg/mL). The final concentration of organic solvent in all incubations is 0.25%. Samples are incubated at 37° C., and NADPH (1 mM final concentration) is added to initiate the reaction. Following 5 minutes of incubation, the reactions are terminated by the addition of methanol containing internal standard then centrifuged at 2500 rpm for 20 minutes at 4° C. Aliquots of the supernatant are diluted with formic acid in deionized water (final formic acid concentration=0.1%) and analyzed for the presence of probe metabolite by liquid chromatography-tandem mass spectrometry or fluorescence, depending on the probe substrate used. Standard in vitro probe substrates for CYP enzymes include: CYP1A2, Phenacetin, 7-ethoxyresorufin; CYP2A6, Coumarin; CYP2B6, Bupropion; CYP2C8, Paclitaxel; CYP2C9, Diclofenac, Tolbutamide, S-Warfarin; CYP2C19, S-Mephenyloin, Omeprazole; CYP2D6, Bufurolol; CYP2E1, Chlorzoxazone; CYP3A4, Midazolam, Testosterone.

Table 3 shows the inhibition of CYP2D6 by six parent compounds and seven PEG conjugates (for desipramine, two sets of conjugates were used: a secondary amine conjugate and a tertiary amine conjugate).

TABLE 3

| Test compounds | CYP2D6 Inhibition of dextromethorphan O-demethylation IC50 (µM) | CYP3A4 Inhibition of midazolam 1-hydroxylation* IC50 (µM) | CYP3A4 Inhibition of testosterone 6β-hydroxylation* IC50 (µM) |
|---|---|---|---|
| Debrisoquine sulfate | 19.5 | >25 | >25 |
| mPEG3-N-debrisoquine | 11.3 | >25 | >25 |
| mPEG6-N-debrisoquine | >25 | >25 | >25 |
| mPEG8-N-debrisoquine | >25 | >25 | >25 |
| Propranolol hydrochloride | 7.5 | >25 | 13.1 |
| mPEG3-O-propranolol | 14.7 | 8.1 | >25 |
| mPEG5-O-propranolol | >25 | 7.6 | >25 |
| mPEG7-O-propranolol | >25 | 10.7 | >25 |
| Timolol maleate | >25 | >25 | >25 |
| mPEG3-O-timolol | 21.7 | >25 | >25 |
| mPEG5-O-timolol | >25 | >25 | >25 |
| mPEG7-O-timolol | >25 | >25 | 10.9 |
| Hydroxyzine dihydrochloride | 3.9 | 20.9 | >25 |
| mPEG3-hydroxyzine | 9.7 | 7.3 | 22.3 |
| mPEG5-hydroxyzine | 11.5 | 7.9 | >25 |
| mPEG7-hydroxyzine | 16.4 | 10.4 | >25 |
| Diphenhydramine hydrochloride | 6 | >25 | 16.9 |
| mPEG3-N-diphenhydramine | 2.6 | 16.4 | >25 |
| mPEG4-N-diphenhydramine | 9.2 | 13.1 | >25 |
| mPEG5-N-diphenhydramine | >25 | 10.8 | >25 |
| mPEG6-N-diphenhydramine | >25 | 7.5 | >25 |
| mPEG7-N-diphenhydramine | >25 | 8 | >25 |
| Desipramine hydrochloride | 2.58 | >25 | >25 |
| mPEG3-desipramine | 2.47 | 14 | >25 |
| mPEG5-desipramine | 15.4 | 13.3 | >25 |
| mPEG8-desipramine | >25 | 13.5 | >25 |
| mPEG3-NH-desipramine | 1.47 | 17.9 | >25 |
| mPEG7-NH-desipramine | >25 | 9.51 | >25 |

Propanolol ($IC_{50}$=7.5 µM), hydroxyzine ($IC_{50}$=3.9 µM), and diphenhydramine ($IC_{50}$=6.0 µM) were inhibitors of CYP2D6, and their PEGylated derivatives displayed less inhibition of CYP2D6 to varying degrees. Debrisoquine ($IC_{50}$=19.5 µM) and timolol ($IC_{50}$>25 µM) were minor inhibitors of CYP2D6, and their PEGylated compounds inhibit CYP2D6 dextromethorphan metabolism to a lesser degree.

With respect to the preparation of mPEGn-N-debrisoquine, acetonitrile (8 mL) and debrisoquin were added in a pressurized reaction vessel. Then a NaOH solution (120 mg NaOH dissolved in 1 mL water) was added until the solution becomes clear. Finally, mPEGn-Br (250 mg) was added to the mixture and a nitrogen atmosphere is introduced into the pressurized vessel. The reaction is allowed to progress overnight at 70° C. and is monitored by analytical HPLC. Upon reaction completion, dichloromethane (200 mL) is added and the aqueous and organic layers separated using a separatory funnel. The organic phase was removed and the remaining aqueous phase was further extracted with dichloromethane (3×150 mL). The combined organic layers were dried over sodium sulfate and the solvent removed under reduced pressure. The resulting crude products were purified.

With respect to the preparation of mPEGn-O-propranolol, 60% sodium hydride (0.40 g, 0.01 mol) was placed into a 100 mL flask, and washed with hexanes (3×2 mL). The residual hexanes were removed under vacuum. The residue was taken up in anhydrous THF (10 mL). Propranolol hydrochloride (0.50 g, 1.69 mmol) in THF (10 mL) was then added all at once, followed by mPEGn-Br (0.77 g, 3.38 mmol, 2.0 equivalents) in THF (15 mL). The cloudy mixture was stirred under nitrogen and heated. After about 20 hours, the reaction was stopped. The mixture was concentrated under reduced pressure and then purified.

With respect to the preparation of mPEGn-O-timolol, timolol (0.4 mmol, 140.0 mg), was dissolved in 5 ml anhydrous THF. Sodium hydride (60% dispersion in mineral oil) (0.8 mmol, 52.8 mg) was added to timolol solution and the solution was stirred at room temperature for ten minutes. mPEGn-Br (1.4 equivalents) was dissolved in 0.50 ml THF and the solution was added to reaction mixture. The reaction mixture was stirred 16 hours at room temperature. The reaction mixture was washed with an excess amount of saturated ammonium chloride solution and the product was extracted in dichloromethane (53×50 mL). The organic phases were combined and the solvent was removed under reduced pressure. The resulting crude product was purified.

With respect to the preparation of mPEGn-desipramine, desipramine (2.00 g, 6.60 mmol) was dissolved in methanol (40 mL) and saturated NaHCO$_3$ (80 mL). The reaction was kept at room temperature for 30 minutes and the solution pH was >10. After the methanol was removed under reduced pressure, the aqueous solution was extracted with DCM (50 mL+25 mL×2). The combined organic layers were dried over Na$_2$SO$_4$, filtered, and the solvent removed under reduced pressure. The resulting residue was solidified overnight by vacuum drying and a yellowish sample (1.79 g, >100% yield) was obtained. The free desipramine thus obtained was dissolved in DMF (3.2 mL). NaH (46 mg, 1.92 mmol, 3 eq) was added and the reaction was kept at room temperature for five minutes mPEG$_n$-Br (283 µL, 1.28 mmol, 2 eq) was added and the reaction was allowed to stir overnight (16 hours). Upon obtaining a clear solution, the reaction was quenched with NH$_4$Cl (50 mL) and extracted with DCM (15 mL×3). The organic phases were combined and dried over Na$_2$SO$_4$. After filtration, DCM was evaporated and DMF was rotavapped under high vacuum. The resulting residue was purified.

With respect to the preparation of mPEGn-NH-desipramine, in a MCE microwave reaction tube, iminodibenzyl (1.95 g, 10 mmol) was suspended in toluene (10 mL). The solution was protected under N$_2$. After 1-bromo-3-chloropropane (1.48 mL, 15 mmol) was added, the solution became clear at room temperature. LiNH$_2$ (276 mg, 12 mmol) was then added and the tube was sealed. The microwave reaction was carried out at 120° C. over 18 hours. The reaction was quenched with a saturated aqueous NaHCO$_3$ solution and extracted with EtOAc (50 mL×2). The combined organic phases were dried over MgSO$_4$ and the solvent removed under reduced pressure. The iminodibenzyl alkylation product mixture was added to a microwave reaction tube together with mPEGn-NH$_2$ (340 µL, 1.0 mmol). K$_2$CO$_3$ (207 mg, 1.5 mmol) was added with H$_2$O (1 mL). The starting material was suspended at the top layer of the water phase—stirring was difficult before heating occurred. The microwave reaction was carried out at 120° C. over two hours. The reaction was monitored by TLC for the disappearance of mPEG-NH$_2$. The reaction was then diluted with an aqueous NaHCO$_3$ solution and extracted with DCM (10 mL×3). The combined organic phases were dried over MgSO$_4$, filtered, and the solvent removed under reduced pressure. The resulting residue was purified.

The PEGylated compounds inhibit the midazolam-binding site of CYP3A4 more than the parent, unconjugated compounds. For the testosterone-binding site of CYP3A4, the PEGylated compounds inhibit either more than the parent compounds (debrisoquine, timolol, and hydroxyzine) or less than the parent compounds (propranolol and diphenhydramine).

Through an increase in IC$_{50}$ values, the data reveal a PEG size-dependent decrease in affinity for CYP2D6 inhibition. A decrease in IC$_{50}$ values was observed for the midazolam binding site, indicating an increased affinity of the PEG conjugates for CYP3A4. Taken together, the results reveal a decrease in affinity for CYP2D6, and an increase in affinity for CYP3A4, for PEGylated compounds versus the parent, unconjugated molecules.

It should be understood that all modifications or alternatives equivalent thereto are within the spirit and scope of the invention as set forth in the appended claims. The combination of particular aspects of the various embodiments of the invention is included in the scope of the invention. All patents, patent applications, and other scientific or technical writings referred to anywhere herein are incorporated by reference in their entirety.

We claim:

1. A method of treating a human subject having a disease treatable with a CYP2D6 bioactive drug, the method comprising:
   (i) identifying a human subject as being a CYP2D6 intermediate, extensive or ultrarapid metabolizer; and
   (ii) altering the metabolic pathway of a CYP2D6 bioactive drug comprising administering to the subject identified in (i), an effective amount of the CYP2D6 bioactive drug debrisoquine covalently attached at its amino group to a water-soluble oligomer, whereby the debrisoquine covalently attached at its amino group to the water-soluble oligomer is metabolized by CYP3A4 but is not metabolized by CYP2D6; and
   administering an effective amount of celecoxib, a CYP2D6 inhibiting drug;
   and
   whereby interactions between the debrisoquine covalently attached at its amino group to the water-soluble oligomer and celecoxib are reduced as compared to administration of celecoxib and unmodified debrisoquine.

2. The method of claim 1, wherein the water-soluble oligomer is a methoxy end-capped oligo(ethylene oxide) moiety.

3. The method of claim 1, wherein the human subject is identified as being an intermediate metabolizer.

4. The method of claim 1, wherein the human subject is identified as being an ultrarapid metabolizer.

5. The method of claim 2, wherein the methoxy end-capped oligo(ethylene oxide) moiety comprises from 2-10 monomers.

6. The method of claim 5, wherein the methoxy end-capped oligo(ethylene oxide) moiety comprises from 5-8 monomers.

7. The method of claim 5, wherein the methoxy end-capped oligo(ethylene oxide) moiety comprises 5 or 6 monomers.

8. The method of claim 5, wherein the methoxy end-capped oligo(ethylene oxide) moiety comprises 7 or 8 monomers.

9. The method of claim 5, wherein the CYP2D6 bioactive drug is mPEG3-N-debrisoquine.

* * * * *